US010725041B2

(12) United States Patent
Newman et al.

(10) Patent No.: US 10,725,041 B2
(45) Date of Patent: Jul. 28, 2020

(54) METHOD TO BIOENGINEER DESIGNER PLATELETS USING GENE EDITING AND STEM CELL METHODOLOGIES

(71) Applicant: Versiti Blood Research Institute Foundation, Inc., Milwaukee, WI (US)

(72) Inventors: Peter Jay Newman, Bayside, WI (US); Sridhar Rao, Brookfield, WI (US); Nanyan Zhang, Wauwatosa, WI (US); Huiying Zhi, Brookfield, WI (US)

(73) Assignee: VERSITI BLOOD RESEARCH INSTITUTE FOUNDATION, INC., Milwaukee, WI (US)

( * ) Notice: Subject to any disclaimer, the term of this patent is extended or adjusted under 35 U.S.C. 154(b) by 212 days.

(21) Appl. No.: 14/931,321

(22) Filed: Nov. 3, 2015

(65) Prior Publication Data

US 2016/0139124 A1     May 19, 2016

Related U.S. Application Data

(60) Provisional application No. 62/074,870, filed on Nov. 4, 2014.

(51) Int. Cl.
| | |
|---|---|
| *G01N 33/569* | (2006.01) |
| *C12N 15/85* | (2006.01) |
| *C12N 5/078* | (2010.01) |
| *C12N 5/074* | (2010.01) |
| *C12N 15/11* | (2006.01) |

(52) U.S. Cl.
CPC ..... *G01N 33/56977* (2013.01); *C12N 5/0644* (2013.01); *C12N 5/0696* (2013.01); *C12N 15/111* (2013.01); *C12N 15/85* (2013.01); *C12N 2310/20* (2017.05); *C12N 2510/00* (2013.01); *C12N 2800/80* (2013.01)

(58) Field of Classification Search
CPC ............ G01N 33/56977; C12N 15/111; C12N 15/85; C12N 5/0641; C12N 5/0644; C12N 5/0696; C12N 2310/20; C12N 2510/00; C12N 2800/80
See application file for complete search history.

(56) References Cited

U.S. PATENT DOCUMENTS

| | | | |
|---|---|---|---|
| 2014/0271590 A1* | 9/2014 | Feng ...................... | A61K 35/19 424/93.72 |
| 2016/0077089 A1* | 3/2016 | Schawaller ............ | G01N 33/86 435/7.92 |

FOREIGN PATENT DOCUMENTS

| | | | | |
|---|---|---|---|---|
| WO | WO 2014204724 A1 * | 12/2014 | ............... | C12N 9/22 |

OTHER PUBLICATIONS

Sachs et al. "A point mutation in the EGF-4 domain of β3 integrin is responsible for the formation of the Seca platelet alloantigen and affects receptor function." Thromb Haemost. Jan. 2012 ; 107(1): 80-87.*
Rosselló et al. "Mammalian genes induce partially reprogrammed pluripotent stem cells in non-mammalian vertebrate and invertebrate species." Elife. Sep. 3, 2013;2:e00036. (Year: 2013).*
An et al. "High-throughput simultaneous genotyping of human platelet antigen-1 to -16 by using suspension array." Transfusion. 2013;53(11):2722-8.
Aster RH. Studies of the fate of platelets in rats and man. Blood. 1969;34(2):117-28.
Aster et al. "Expression of HLA-B12, HLA-B8, w4, and w5 on platetelets." TransplantProc. 1977;9(4):1695-6.
Bonacossa et al. "Alloimmune thrombocytopenia of the newborn: neurodevelopmental sequelae." Am J Perinatol. 1996;13(4):211-5.
Bussel "Diagnosis and management of the fetus and neonate with alloimmune thrombocytopenia." Journal of thrombosis and haemostasis : JTH. 2009;7 (Suppl 1):253-7.
Bussel et al. "Current approaches to the evaluation and management of the fetus and neonate with immune thrombocytopenia." Seminars in perinatology. 2009;33(1):35-42.
Choi et al. "Generation of mature human myelomonocytic cells through expansion and differentiation of pluripotent stem cell-derived lin-CD34+CD43+CD45+ progenitors." The Journal of clinical investigation. 2009;119(9):2818-29.
Cong et al. "Multiplex genome engineering using CRISPR/Cas systems." Science. 2013;339(6121):819-23.
Curtis "Genotyping for human platelet alloantigen polymorphisms: applications in the diagnosis of alloimmune platelet disorders." Seminars in thrombosis and hemostasis. 2008;34(6):539-48.
Ding et al. "Enhanced efficiency of human pluripotent stem cell genome editing through replacing TALENs with CRISPRs." Cell stem cell. 2013;12(4):393-4.
Dreyfus et al. "Frequency of immune thrombocytopenia in newborns: a prospective study." Immune Thrombocytopenia Working Group. Blood. 1997;89(12):4402-6.
Feng et al. "Scalable generation of universal platelets from human induced pluripotent stem cells." Stem Cell Reports 2014;3(5):817-31.

(Continued)

*Primary Examiner* — Titilayo Moloye
(74) *Attorney, Agent, or Firm* — Quarles & Brady LLP

(57) ABSTRACT

Methods of creating cells expressing specific platelet alloantigens by combining gene editing techniques and cell culture differentiation or expansion techniques employing pluripotent cells, including the steps of transfecting pluripotent cells with a plasmid encoding one or more guide RNAs targeting within a platelet alloantigen target locus and a nuclease in the presence of an HDR repair oligo and culturing the resulting cells to expand their numbers or to create a differentiated cell type of interest.

9 Claims, 6 Drawing Sheets
(6 of 6 Drawing Sheet(s) Filed in Color)
Specification includes a Sequence Listing.

(56) References Cited

OTHER PUBLICATIONS

Gras et al. "HLA-universal platelet transfusions prevent platelet refractoriness in a mouse model." Human gene therapy. 2013;24(12)1018-28.

Giovangrandi et al. "Very early intracranial haemorrhage in alloimmune fetal thrombocytopenia." Lancet. 1990;336(8710):310.

Harrison et al. "Severe neonatal alloimmune thrombocytopenia caused by antibodies to human platelet antigen 3a (Baka) detectable only in whole platelet assays." Transfusion. 2003;43(10):1398-402.

Karginov et al. "The CRISPR system: small RNA-guided defense in bacteria and archaea." Molecular cell. 2010;37(1):7-19.

Kennedy et al. "Development of the hemangioblast defines the onset of hematopoiesis in human ES cell differentiation cultures." Blood. 2007;109(7):2679-87.

Kjeldsen-Kragh et al "A screening and intervention program aimed to reduce mortality and serious morbidity associated with severe neonatal alloimmune thrombocytopenia." Blood. 2007;110(3):833-9.

Lancet et al. "Heavy chain of HLA-A and HLA-B antigens is conformationally labile: a possible role for b2-microglobulin." Proceedings of the National Academy of Sciences of the United States of America. 1979;76(8):3844-8.

Le Toriellec et al. "Safe fetal platelet genotyping: new developments." Transfusion. 2013;53(8):1755-62.

Mali et al. "Cas9 as a versatile tool for engineering biology." Nature methods. 2013;10(10):957-63.

McFarland et al. "Prenatal diagnosis of neonatal alloimmune thrombocytopenia using allele-specific oligonucleotide probes." Blood. 1991;78(9):2276-82.

Metcalfe et al. "Nomenclature of human platelet antigens." Vox Sang. 2003;85(3):240-5.

Mills et al. In: Qu KDBaC-K ed. Methods in Molecular Biology. New York: Springer Science+Business Media; 2014:181-94.

Nakamura et al. "Expandable megakaryocyte cell lines enable clinically applicable generation of platelets from human induced pluripotent stem cells." Cell stem cell. 2014;14(4):535-48.

Nielsen et al. "HL-A immunization and HL-A types in pregnancy." Tissue Antigens. 1972;2(4):316-27.

Newman et al. "The human platelet alloantigens, PIA1 and PIA2, are associated with a leucine33/proline33 amino acid polymorphism in membrane glycoprotein IIIa, and are distinguishable by DNA typing." JClinInvest. 1989;83(5)1778-81.

Ouwehand "The dilemma of screening for antibodies against low-frequency human platelet antigens." Transfusion. 2005;45(3):288-9.

Paluru et al. "The negative impact of Wnt signaling on megakaryocyte and primitive erythroid progenitors derived from human embryonic stem cells." Stem cell research. 2014;12(2):441-51.

Ran et al. "Genome engineering using the CRISPR-Cas9 system." Nature protocols. 2013;8(11):2281-308.

Ran et al. "Double nicking by RNA-guided CRISPR Cas9 for enhanced genome editing specificity." Cell. 2013;154(6):1380-9.

Shen et al. "Efficient genome modification by CRISPR-Cas9 nickase with minimal off-target effects." Nature methods. 2014;11(4):399-402.

Shulman et al. "Immunoreactions involving platelets. VI. Reactions of maternal isoantibodies responsible for neonatal purpura. Differentiation of a second platelet antigen system." The Journal of clinical investigation. 1962;41(5):1059-69.

Si-Tayeb et al. "Generation of human induced pluripotent stem cells by simple transient transfection of plasmid DNA encoding reprogramming factors." BMC developmental biology. 2010;10:81.

Skogen et al. "Rapid determination of platelet alloantigen genotypes by polymerase chain reaction using allele specific primers." Transfusion. 1994;34(11):955-60.

Spencer et al. "Feto-maternal alloimmune thrombocytopenia: a literature review and statistical analysis." The Australian & New Zealand journal of obstetrics & gynaecology. 2001;41(1):45-55.

Sullivan et al. "High-level transgene expression in induced pluripotent stem cell-derived megakaryocytes: correction of Glanzmann thrombasthenia." Blood. 2014;123(5):753-7.

Takahashi et al. "Induction of pluripotent stem cells from adult human fibroblasts by defined factors." Cell. 2007;131(5):861-72.

Thon et al. "Platelet bioreactor-on-a-chip." Blood. 2014; 124 (12):1857-67.

Turner et al. "Prospective epidemiologic study of the outcome and cost-effectiveness of antenatal screening to detect neonatal alloimmune thrombocytopenia due to anti-HPA-1a." Transfusion. 2005;45(12)1945-56.

Van Loghem et al. Serological and genetical studies on a platelet antigen (Zw). Vox Sang. 1959;4(2):161-9.

Vassallo "New paradigms in the management of alloimmune refractoriness to platelet transfusions." Current opinion in hematology. 2007;14(6):655-63.

Wang et al. "One-step generation of mice carrying mutations in multiple genes by CRISPR/Cas-mediated genome engineering." Cell. 2013;153(4):910-8.

Wang et al. "Comparative analysis of human ex vivo-generated platelets vs megakaryocyte-generated platelets in mice: a cautionary tale." Blood. 2015;125(23):3627-36.

Wilcox et al. "Integrin aIIb promoter-targeted expression of gene products in megakaryocytes derived from retrovirus-transduced human hematopoietic cells." Proceedings of the National Academy of Sciences of the United States of America. 1999;96(17):9654-9.

Williamson et al. "The natural history of fetomaternal alloimmunization to the platelet- specific antigen HPA-1a (PIA1, Zwa) as determined by antenatal screening." Blood. 1998;92(7):2280-7.

Yu et al. "Induced pluripotent stem cell lines derived from human somatic cells." Science. 2007;318(5858):1917-20.

\* cited by examiner

Figure 6

Predicted Off-Target Sites for Guides #1 and #2

| | Chromosome | Position | Strand | Sequence | Mismatches | Fw primer | Rev Primer | PCR product size (bp) |
|---|---|---|---|---|---|---|---|---|
| Guide#1 | 17 | 45360677 | | GAGTTCCAGAGACCTAGACCTATA (SEQ ID NO:23) | 0 | | | |
| OT1-1 | 15 | -76441227 (76441232-76441254) | - | CAGTTCTGCAATCAGAGCTAAAG (SEQ ID NO:24) | 3 [1,5,7] | GAGAACCA TCAACCCA ATGC (SEQ ID NO:25) | GTGTATGGCAGTT TGTCCAC (SEQ ID NO:26) | 506 |
| OT1-2 | 9 | +94270131 (94270133-94270155) | + | AGGTTCAGTAATCAGAGCTATGG (SEQ ID NO:27) | 3 [2,5,9] | GCCATAAA GTGGGATC ATTTG (SEQ ID NO:28) | ACCATAGGTCCT CGATGT (SEQ ID NO:29) | 519 |
| OT1-3 | 16 | +26565066 (26565068-26565090) | + | CAGGCCAGCACCAGAGCTATGG (SEQ ID NO:30) | 3 [1,4,12] | TCAATGCT AAACAACG GCAC (SEQ ID NO:31) | GCTGCTGATCTGA AAGGGTA (SEQ ID NO:32) | 520 |
| OT1-4 | 2 | -169381174 (169381203-169381179) | - | AAATACCAACCATCAGAGCTACAG (SEQ ID NO:33) | 4 [3,4,8,10] | CAACTGAG CCTTCCTA CCA (SEQ ID NO:34) | AGAGAGGAATTG AGACACC (SEQ ID NO:35) | 546 |
| OT1-5 | 1 | -69597324 (69597351-69597329) | - | AAATACAGCAATCAGAGCAAGAG (SEQ ID NO:36) | 3 [3,5,19] | ATTAAAGC TTCTGCTG GCGA (SEQ ID NO:37) | TGATACTCCACTTG ACAACTC (SEQ ID NO:38) | 452 |
| Guide#2 | 17 | +45360709 | + | TGTCCTTACAGAGCCTGCCTCAGG (SEQ ID NO:39) | 0 | | | |
| OT2-1 | 10 | +45194794 (45194796-45194818) | + | TCTCCTACATGCCCTGCCTCAGG (SEQ ID NO:40) | 3 [2,5,10] | CTGTCTCTG CTGCACAT CTA (SEQ ID NO:41) | GTTCAGGTGGAGA CAGGAAT (SEQ ID NO:42) | 547 |
| OT2-2 | 20 | -10715445 (10715477-10715450) | - | TGTCTTTCAGCCCCTGCCTCAGG (SEQ ID NO:43) | 2 [7,11] | TAAGACCA TATGGACA TGGAGA (SEQ ID NO:44) | GACTAGCAAATGG CTGGAACA (SEQ ID NO:45) | 605 |
| OT2-3 | 17 | -63100895 (63100922-63100900) | - | GGTTTTTCAGGCCCTGCCTCCAG (SEQ ID NO:46) | 3 [1,4,7] | GAGTTTGC TGTGCAGA GATG (SEQ ID NO:47) | TGCTTAAGTGTGG GCCTTTA (SEQ ID NO:48) | 455 |
| OT2-4 | 1 | +25355562 (25355564-25355586) | + | GGTTTTTCAGGCCCTGCCTCAAG (SEQ ID NO:49) | 3 [1,4,7] | AAAGAGAG ATGAGCTC GTGG (SEQ ID NO:50) | TTTCAAGAGTGGA GTGGCTT (SEQ ID NO:51) | 430 |
| OT2-5 | 3 | +173333048 (173333050-173333072) | + | TGTCCTGGAGGCCCTGCCTCAGG (SEQ ID NO:52) | 3 [5,7,8] | GAAATTCTT TGGCCACC TCC (SEQ ID NO:53) | CACAGTGCCAAAT ATCAGCA (SEQ ID NO:54) | 511 |

US 10,725,041 B2

METHOD TO BIOENGINEER DESIGNER PLATELETS USING GENE EDITING AND STEM CELL METHODOLOGIES

CROSS-REFERENCE TO RELATED APPLICATIONS

This application claims the benefit of U.S. Provisional Patent Application Ser. No. 62/074,870 filed Nov. 4, 2014.

STATEMENT REGARDING FEDERALLY SPONSORED RESEARCH

This invention was made with government support under Grant No. P01-HL44612 awarded by the National Institutes of Health. The U.S. Government has certain rights in this invention.

BACKGROUND

Platelet alloantigens are substances that induce the production of alloantibodies when platelets bearing such antigens are infused into patients who lack the specific alloantigen. Immune responses to platelet alloantigens are involved in the pathogenesis of several clinical syndromes including neonatal alloimmune thrombocytopenia, post-transfusion purpura, and refractory responses to platelet transfusion. In addition, immune thrombocytopenia can be an unusual complication of a type of graft-versus-host disease in which donor lymphocytes make alloantibodies specific for the platelets produced by the recipient of an organ allograft.

Patients can lack a particular platelet-associated antigen altogether because they have defective alleles of the gene encoding the antigen. Such patients can make antibodies against platelets of virtually all donors that bear the platelet-associated antigen. For example, patients with Bernard-Soulier syndrome, who lack platelet GPIb-V-IX, or patients with Glanzmann thrombasthenia, who lack expression of GPIIb (CD41) and GPIIIa (CD61), can be induced to make broadly-reactive antiplatelet antibodies. Also, several percent of Japanese and approximately 0.3 percent of Caucasians are deficient in CD36, one of the major platelet glycoproteins of platelets that also is known as GPIV. Because these patients lack a platelet antigen, they can develop antiplatelet antibodies specific for the deficient platelet protein after receiving transfusions of platelets from normal donors or after pregnancy. More commonly, platelet-specific alloantigens result from genetic polymorphism in genes encoding functional platelet proteins. These alloantigens first were defined by antiplatelet antibodies discovered in the sera of multiparous females who gave birth to infants with neonatal thrombocytopenia. Many of these subsequently were found to recognize allotypic determinants of platelet-associated membrane glycoproteins, such as GPIIb/IIIa (CD41/CD61). Each of these allotypic determinants may be generated by only a single amino acid substitution in a major platelet-associated glycoprotein. However, it is possible that glycosylation may contribute to or influence the expression of certain Human Platelet Alloantigenic (HPA) epitopes, such as those associated with human platelet antigen 3 (HPA-3). In any case, these amino acid substitutions generally do not appear to affect the function of platelets in vitro. However, it is conceivable that the genetic polymorphism in platelet glycoproteins may be associated with more subtle differences in platelet physiology that can contribute to the relative risk for thrombosis and/or atherosclerosis. (Williams Hematology, Chapter 138)

The human leukocyte histocompatibility antigens, HLA, are polymorphic cell surface glycoproteins that present antigen peptide fragments to T-cell receptors. HLA antigens are encoded by multiple, closely linked genes, located in a 4-Mb region of DNA on chromosome 6, that comprise the major histocompatibility complex (MHC) and play a central role in the regulation of immune responses. In general, the MHC genes are inherited as a single unit in simple Mendelian fashion. The products of the MHC HLA-A, HLA-B, and HLA-C genes are called class I antigens. Class I antigens are expressed on essentially all tissues in the body and present small peptide fragments to CD8+ T cells. (Williams Hematology, Chapter 138)

There are six major groups of HLA antigens: HLA-A, HLA-B, HLA-C, HLA-DR, HLA-DQ, and HLA-DP. These groups are divided into classes of antigens designated as class I and class II, representing the two types of HLA molecules. The HLA-A, HLA-B, and HLA-C antigens are the class I antigens. The HLA-DR, HLA-DQ, and HLA-DP antigens are the class II antigens. (Williams Hematology, Chapter 138)

In addition to the HLA antigens, platelets also express glycoproteins that can be recognized by autoantibodies or by antibodies made by recipients of platelet transfusions. The latter are due to platelet alloantigens that reflect polymorphism in the genes encoding major platelet glycoproteins. Immune responses to platelet alloantigens are involved in the pathogenesis of several clinical syndromes, including neonatal alloimmune thrombocytopenia, post-transfusion purpura, and refractory responses to platelet transfusion. (Williams Hematology, Chapter 138)

The inventors have discovered a method of creating human platelets expressing specific HPA isotypes utilizing CRISPR/Cas9 gene editing methods and laboratory cell culture techniques. Deletion of the $\beta_2$ microglobulin gene offers distinct practical advantages that will be outlined in the description of the invention.

The inventors have discovered a method to generate human platelets that express any minor or major HPA that is desired, so called "designer platelets". After demonstrating that one can convert $Pl^{A1}$ to $Pl^{A2}$ in DAMI cells, the inventors have most recently shown this conversion in human induced pluripotent stem (iPS) cells which can be differentiated into megakaryocytes and then platelets using methods known in the art. Our initial anticipated use will be the development of a new platform for rapid flow cytometric detection of rare platelet antigens. This will be made useful and easier than antigen capture ELISA test (ACE) or modified antigen capture ELISA test (MACE) because we will also knock out $\beta_2$ microglobulin in the iPS cells so that anti-HLA antibodies in maternal or patient sera will have no Class I targets to bind to, hopefully simplifying the assay and lowering back-ground.

In concept, it would be very useful to have such a panel for laboratory testing. Even though the market might be small, you could argue that the project might provide proof-of principal for future studies to express rare RBC antigens (of which there are many). Right now, reference blood banks maintain frozen RBC panels expressing various low frequency RBC antigens or (equally important) lacking high frequency (public) antigens and they thaw them out when they need to check specificity of an unknown antibody in a patient. Producing "designer RBCs", that look identical to physiologic RBC's, could be a serious technical challenge because the cultured cells need to shed their nucleus, among other things and techniques to do this are not currently completely finalized. However, one could express the rare RBC antigens in nucleated RBC's, anucleated RBC's, platelets, iPS cells, or iPS cell and then use these cell types as laboratory controls and sources of these rare antigens.

An additional use of iPS—derived designer platelets will be to provide rare platelet types for transfusion. This will require the use of a platelet bioreactor. The commercial use of platelet bioreactors is not yet commonplace. However, one advantage of this strategy, is the gene editing arm of the technology, which allows you to make platelets of specific HPA types. The therapeutic use of platelets that lack specific HLA antigens or express matching HLA antigens could be a solution to various forms of platelet refractoriness. The platelets would be group ABO negative or group O, to rule out issues with ABO compatibility. HPA-1a-negative platelets might be useful for the most common form of NAIT. Platelets matched for other HPA antigens are occasionally useful in immunized thrombocytopenic patients.

BRIEF SUMMARY OF THE INVENTION

In one embodiment, the present invention is a method of creating cells expressing specific platelet or red blood cell alloantigens by combining gene editing techniques and cell culture techniques employing pluripotent cells, the method comprising the steps of editing a plutipotent cell so that the cell expresses the alloantigen of interest and culturing the cell to expand or create a differentiated cell type. In a preferred embodiment, the cells are further edited by removal of HLA class I antigens.

In a preferred embodiment, the method comprises the steps of (a) combining one or more guide RNAs targeting within a platelet alloantigen target locus; (b) adding a repair template comprising a mutation in the target locus flanked by a homology arm on each side, wherein the template may additionally include a diagnostic restriction enzyme site at the target locus; (c) ligating the guide sequence of step (b) into a plasmid which also expresses a nuclease and, optionally, a selectable marker or a reporter gene; (d) transfecting pluripotent cells with the plasmid of step (c) in the presence of an HDR repair oligo; (e) cloning and testing the resulting reporter positive clones for expression of the alloantigen target of interest; and (f) culturing the resulting cells to expand their numbers or to create a differentiated cell type of interest.

In another preferred embodiment, the method comprises the steps of (a) combining one or more guide RNAs targeting within a red cell alloantigen target locus; (b) adding a repair template comprising a mutation in the target locus flanked by a homology arm on each side, wherein the template may additionally include a diagnostic restriction enzyme site at the target locus; (c) ligating the guide sequences of step (b) into a plasmid which also expresses a nuclease and, optionally a selectable marker or a reporter gene; (d) transfecting pluripotent cells with the plasmid of step (c) in the presence of an HDR repair oligo; (e) cloning and testing the resulting reporter positive clones for expression of the alloantigen target of interest; and (f) culturing the resulting cells to expand their numbers or to create a differentiated cell type of interest.

Preferred embodiments of the present invention include the step of further editing the cells in step (a) by removal of HLA class I antigens, preferably by genetic removal of the $\beta_2$ microglobulin gene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 shows the sequences and positions of on-target and possible off-target sites for gRNA1 and gRNA2. OT1: Off-target site for gRNA1. OT2: Off-target site for gRNA2. The primers for PCR amplification of off-target regions and expected size of PCR products are also listed.

DESCRIPTION OF THE INVENTION

In General

Figure 1:
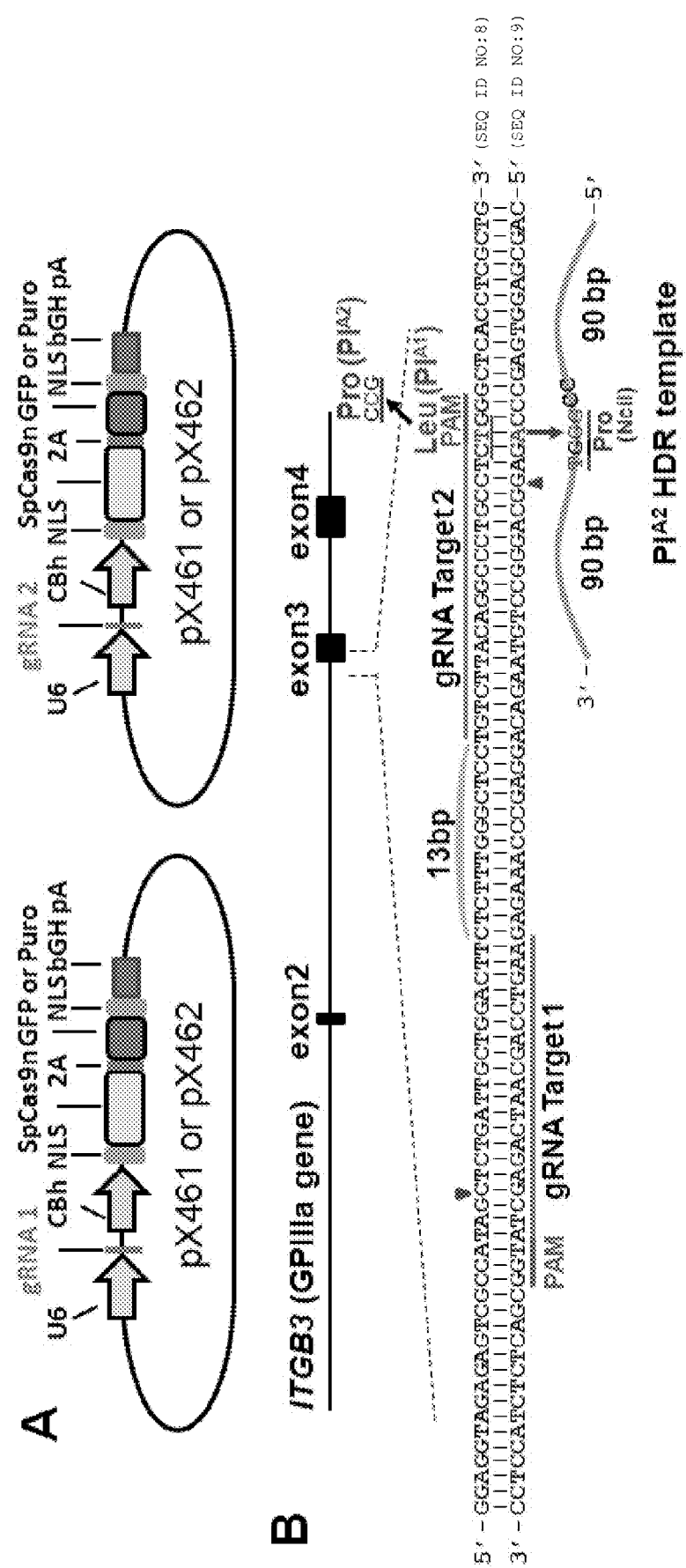
FIG. 1A: Depicts the strategy used to convert the $Pl^{A1}$ allelic form of GPIIIa to $Pl^{A2}$, specifically, a pair of 20 bp gRNAs were designed to target the single-stranded nuclease, Cas9n, to opposite strands of the ITGB3 gene with a 13 bp offset surrounding the $Pl^A$ polymorphic site. The gRNAs were cloned into the BbsI site of the CRISPR vectors px461 or px462, which encode green fluorescent protein (GFP) or a puromycin-resistance gene, respectively, as well as Cas9n. The use of two different guides to direct the Cas9n nickase to nearby sites at this locus significantly reduces the incidence of off-target mutations relative to that incurred using a single guide RNA and the double-strand nuclease Cas9 (49, 50).
FIG. 1B: Depicts the strategy used to convert the $Pl^{A1}$ allelic form of GPIIIa to $Pl^{A2}$, specifically, schematic illustration of the ITGB3 locus, showing the location of the two gRNA binding sites (orange bars) and the protospacer adjacent motifs (PAM) sequences (magenta), positioned 53 bp and 0 nucleotide upstream of the T>C mutation site, necessary to guide Cas9n to its cleavage site (red arrow heads). A 181 bp $Pl^{A2}$ HDR template was designed to introduce the Leu→Pro amino acid polymorphism. The T>C mutation responsible for the $Pl^{A1}/Pl^{A2}$ polymorphism (highlighted in red) is flanked by 90 nucleotide homology arms, and creates an NciI site at the target locus that can be used for genotyping (13). The HDR template also contains two silent mutations (highlighted in blue) to prevent re-cleavage by Cas9n (see Methods).

Human platelet alloantigens (HPAs) reside on functionally important platelet membrane glycoproteins and are caused by single nucleotide polymorphisms in the genes that encode them. Antibodies that form against HPAs are responsible for several clinically important alloimmune bleeding disorders, including fetal and neonatal alloimmune thrombocytopenia, posttransfusion purpura, and multitransfusion platelet refractoriness.

The HPA-1a/HPA-1b alloantigen system, also known as the Pl$^{A1}$/Pl$^{A2}$ polymorphism, is the most frequently implicated HPA among Caucasians, and a single C29523T nucleotide substitution, resulting in a Leu33Pro amino acid polymorphism within the PSI domain of the integrin β3 subunit (platelet glycoprotein IIIa) was shown 25 years ago to be responsible for generating the HPA-1a/HPA-1b alloantigenic epitopes. Like other low-frequency alloantigens, HPA-1b/b platelets are relatively rare in the population, and therefore often difficult to obtain for purposes of transfusion therapy and diagnostic testing.

The platelet alloantigen system has had a variety of nomenclature styles over the years since it was first documented by one of the inventors on this application. The human platelet alloantigen or HPA nomenclature is the most widely used today. However, historically, the antigens were known by names such as Pla, Pen, Bak, Br, Gov, and others. Certain of the alloantigen mutations occur more frequently in nature, leading to a higher incidence of clinical issues associated with that polymorphism.

Below is a listing of HPA alloantigens suitable for the present invention, the glycoprotein impacted, and their genetic basis:

| Antigen | Glycoprotein | Hugo Gene Nomenclature | Chromosome | Nucleotide Change | Precursor | Mature Protein |
| --- | --- | --- | --- | --- | --- | --- |
| HPA-1 | GPIIIa | ITGB3 | 17 | 176T > C | L59P | L33P |
| HPA-2 | GPIba | GP1BA | 17 | 482C > T | T161M | T145M |
| HPA-3 | GPIIb | ITGA2B | 17 | 2621T > G | I874S | I843S |
| HPA-4 | GPIIIa | ITGB3 | 17 | 506G > A | R169Q | R143Q |
| HPA-5 | GPIa | ITGA2 | 5 | 1600G > A | E534K | E505K |
| HPA-6w | GPIIIa | ITGB3 | 17 | 1544G > A | R515Q | R489Q |
| HPA-7w | GPIIIa | ITGB3 | 17 | 1297C > G | P433A | P407A |
| HPA-8w | GPIIIa | ITGB3 | 17 | 1984C > T | R662C | R636C |
| HPA-9w | GPIIb | ITGA2B | 17 | 2602G > A | V868M | V837M |
| HPA-10w | GPIIIa | ITGB3 | 17 | 263G > A | R88Q | R62Q |
| HPA-11w | GPIIIa | ITGB3 | 17 | 1976G > A | R659H | R633H |
| HPA-12w | GPIbb | GP1BB | 22 | 119G > A | G40E | G15E |
| HPA-13w | GPIa | ITGA2 | 5 | 2483C > T | T828M | T799M |
| HPA-14w | GPIIIa | ITGB3 | 17 | 1909_1911delAAG | K637del | K611del |
| HPA-15 | CD109 | CD109 | 6 | 2108C > A | S703Y | S682Y |
| HPA-16w | GPIIIa | ITGB3 | 17 | 497C > T | T166I | T140I |
| HPA-17w | GPIIIa | ITGB3 | 17 | 662C > T | T221M | T195M |
| HPA-18w | GPIa | ITGA2 | 5 | 2235G > T | Q745H | Q716H |

-continued

| Antigen | Glyco-protein | Hugo Gene Nomenclature | Chromo-some | Nucleotide Change | Precursor | Mature Protein |
|---|---|---|---|---|---|---|
| HPA-19w | GPIIIa | ITGB3 | 17 | 487A > C | K163Q | K137Q |
| HPA-20w | GPIIb | ITGA2B | 17 | 1949C > T | T650M | T619M |
| HPA-21w | GPIIIa | ITGB3 | 17 | 1960G > A | E654K | E628K |
| HPA-22bw | GPIIb | ITGA2B | 17 | 584A > C | K195T | K164T |
| HPA-23bw | GPIIIa | ITGB3 | 17 | 1942C > T | R648W | R622W |
| HPA-24bw | GPIIb | ITGA2B | 17 | 1508G > A | S503N | S472N |
| HPA-25bw | GPIa | ITGA2 | 5 | 3347C > T | T1116M | T1087M |
| HPA-26bw | GPIIIa | ITGB3 | 17 | 1818G > T | K606N | K580N |
| HPA-27bw | GPIIb | ITGA2B | 17 | 2614C > A | L872M | L841M |
| HPA-28bw | GPIIb | ITGA2B | 17 | 2311G > T | V771L | V740L |
| HPA-29bw | GPIIIa | ITGB3 | 17 | 98C > T | T33M | T7M |

Our examples below disclose one embodiment of the present invention. As a first step in producing designer platelets expressing low-frequency human platelet alloantigens, we employed a CRISPR/Cas9 RNA-guided nicking nuclease system to transform megakaryocyte-like cells expressing the Leu33 allele of integrin β3 to the Pro33 form. Two different guide RNAs that target the ITGB3 gene with a 13-base pair offset 53 bases and 0 nucleotides upstream of the C/T polymorphism site were designed and cloned into plasmids that co-express GFP as well as a mutated form of Cas9 that nicks only one strand of DNA (Cas9n). Such a double-nicking strategy has been shown in other systems to increase the specificity of gene targeting while minimizing off-target effects.

A 200 bp single-stranded DNA oligonucleotide encompassing the single base C29523T mismatch was also synthesized to be used for homology-directed repair (HDR) of the endogenous ITGB3 gene sequence. The HDR oligo was then transfected, together with the two plasmids encoding the guide RNAs+Cas9n+GFP, into megakaryocyte-like DAMI cells. Twenty-four hours post-transfection, GFP positive cells were sorted by flow cytometry and isolated as single clones.

Surveyor endonuclease assays revealed that ~30% of the GFP positive clones had been cleaved at the expected location, indicating efficient double nicking directed by the pair of guide RNAs. Additionally, two out of twenty seven isolated clones had incorporated the HDR repair template, as reported by a diagnostic NciI restriction enzyme site that is specific for the T29523-bearing HPA-1b allele. Sequence analysis further confirmed conversion of C29523 to T in these two clones. Finally, Western blotting using HPA-1b-specific human alloantisera verified that these DAMI cells now expressed the HPA-1b (Pl$^{A2}$) alloantigenic epitope. Taken together, these results establish that the CRISPR/Cas system can be successfully employed to genetically edit this and other clinically-important HPAs in human cells. Application of this technology for the generation of alloantigen-specific human induced pluripotent stem cells holds great potential as a general tool for producing designer platelets for diagnostic and therapeutic use.

Embodiments of the Present Invention

In one embodiment, the present invention is the creation of designer platelets or red blood cells via use of gene editing and pluripotent cell culture techniques. In a broad example of the present invention, one would use any gene editing technique to insert an alloantigen of interest in a pluripotent cell and culture and/or differentiate the cell to create the cell type desired. In a preferred embodiment, the cells would be manipulated to be devoid of HLA class I molecules.

In one embodiment, the present invention is a method to create alloantigen-specific platelets using CRISPR/Cas 9 gene editing strategies. The method relies upon existing CRISPR/Cas9 methods in combination with existing pluripotent cell culture methods. In the most preferred embodiment, the cells would be additionally edited to remove the β$_2$ microglobulin gene responsible for expression of HLA on the surface of platelets. The resulting platelets would be useful in laboratory testing or transfusion.

Cells devoid of HLA would be especially useful in diagnostic testing which seeks to determine the presence of patient antibody to platelet alloantigens. In current methods, multiple sources of platelets carrying varying HLA types need to be used to rule out potential cross reactions of patient antibody with the specific platelet alloantigen versus antibodies to HLA on the surface of the platelet. These novel cells devoid of HLA would offer a benefit to simplify laboratory testing.

The inventors have discovered a method of creating platelets expressing specific platelet alloantigens ("designer platelets") by combining gene editing techniques, preferably CRISPR/CAS-9 gene editing techniques, and cell culture techniques employing pluripotent cells, such as iPS or DAMI cells. In one embodiment, the method comprises the steps of: a) combining two guide RNAs targeting ITGB3 gene around a platelet alloantigen locus of interest, such as the Pl$^{A1}$ locus; b) adding a repair template which carries the targeted mutation flanked by a homology arm on each side which creates a restriction enzyme site, preferably an NciI site, at the target locus; c) ligating the guide sequences into a plasmid which also expresses a nuclease capable of cleaving double stranded nucleotides, such as Cas9n, and a reporter gene, such as GFP; d) transfecting pluripotent cells, such as iPS cells, or DAMI cells with the nuclease/guide RNA plasmids in the presence of the HDR repair oligo; e) cloning, expanding and testing the resulting reporter-positive clones for expression of the alloantigen transgene of interest; and f) culturing the resulting cells in an appropriate developmental manner so that platelets are expressed in the culture.

In a preferred embodiment, the cells are genetically manipulated to express the platelet antigen of interest and would be additionally manipulated to be devoid of HLA class I molecules. This is advantageous to rule out issues of cross-reactivity with antibodies from a patient sample or other issues of HLA compatibility in a patient. One practical way to accomplish this embodiment would be to first produce the pluripotent or DAMI cell of interest that has been manipulated to have the $\beta_2$ microglobulin gene of HLA (responsible for HLA expression) removed. The cells could then be then further edited to express the platelet isotypes of interest. $\beta_2$ microglobulin guide RNAs are available commercially from sources such as Santa Cruz Biotechnologies and, thus, $\beta_2$ microglobulin deficient cells can be produced by following manufacturer instructions.

In one preferred embodiment, one would use pluripotent or iPS cell growth and differentiation conditions that favored the myeloid or megakaryocytic lineages. By using a cell type that is a precursor to red cells or platelets, one could better reproduce the carbohydrate glycosylation patterns of the surface glycoproteins of antigenic interest, thereby creating an epitope that more closely resembles naturally occurring alloantigens.

In another embodiment, one could delete the $\beta_2$ microglobulin gene of HLA and add the platelet isotype of interest at the same time during the gene editing process. Briefly, the method comprises the steps of: a) combining two guide RNAs targeting ITGB3 gene around a platelet alloantigen locus, such as the Pl$^{A1}$ locus, along with one or more guide RNAs targeting the areas flanking the $\beta_2$ microglobulin gene of HLA; b) adding the repair template which carries the targeted mutation flanked by a homology arm on each side which creates an at the target locus; c) ligating the guide sequences into a plasmid which also expresses a nuclease, such as Cas9n, and a reporter gene, such as GFP; d) transfecting iPS or DAMI cells with the nuclease/guide RNA plasmids in the presence of the HDR repair oligo; e) cloning, expanding and testing the resulting reporter positive clones for expression of the alloantigen transgene of interest and the deletion of the $\beta_2$ microglobulin gene; and f) culturing the resulting cells so that the designer platelets are expressed in the culture.

In another embodiment, the invention is a method of creating "Designer Red Cells" utilizing the same gene editing approach. Red cells comprise a variety of antigens on their surface which include ABO, RhD, and the following:

RhCE: C(RH2), E(RH3), c(RH4), e(RH5), CW(RH8), V(RH10), hrS(RH19), VS(RH20), hrB(RH31)

Kell: K(KEL1), k(KEL2), Kpa(KEL3), Kpb(KEL4), Jsa (KEL6), Jsb(KEL7)

Kidd: Jka(Jk1), Jkb(Jk2), JKB_null(IVS5-1a), JKB_null (871C)

Duffy: Fya(FY1), Fyb(FY2), FYB_GATA, FYB[265T]_FYX

MNS: M(MNS1), N(MNS2), S(MNS3), s(MNS4), U(MNS5), Mia(MNS7)

Diego: Dia(DI1), Dib(DI2)

Dombrock: Doa(DO1), Dob(DO2), Hy(DO4), Joa(DO5)

Colton: Coa(CO1), Cob(CO2)

Cartwright: Yta(YT1), Ytb(YT2)

Lutheran: Lua(LU1), Lub(LU2)

Briefly, the method comprises the steps of: a) combining two guide RNAs targeting one or more of the above-listed red cell genes; b) adding the repair template which carries the targeted mutation flanked by a homology arm on each side which creates a restriction site, such as an NciI site, at the target locus; c) ligating the guide sequences into a plasmid which also expresses a nuclease and a reporter gene such as GFP; d) transfecting pluripotent cells or DAMI cells with the nuclease/guide RNA plasmids in the presence of the HDR repair oligo; e) cloning, expanding and testing the resulting reporter positive clones for expression of the alloantigen transgene(s) of interest; and f) culturing the resulting cells in a developmentally suitable manner so that designer red cells are expressed in the culture.

In another embodiment, the invention is a method of using the resulting pluripotent cells cells, cell derivatives, designer red cells, or designer platelets in the laboratory as reagents to test patient blood samples for the presence of antibody to the expressed alloantigens or as controls for nucleic acid testing of those genes.

In another embodiment, the invention is a method of creating designer platelets for use in transfusion of patients with platelets of a specific isotype. For example, one could transfuse gene-edited, alloantigen specific designer platelets or their progenitor cells into patients for the purpose of correcting thrombocytopenia and similar bleeding disorders.

In another embodiment, the invention is a method of creating designer platelets or red cells for use in diagnostic testing through solubilizing a gene-edited pluripotent cell or progeny cells with a detergent and linking those solubilized alloantigen proteins to a solid surface such as a bead or plate. This solid surface, most preferably a bead, carrying the platelet alloantigen would serve as a platelet for the purpose of detection platforms such as flow cytometry and others. A solid surface, such as an ELISA plate, would serve as a platelet for the purpose of detection platforms such as ELISA and others. A variety of detergents could be used that include both non-ionic or ionic detergents that onecould find by empirical testing. Common detergents used for this purpose include CHAPS, Tween® 20, Triton X 100 and others.

A preferred method uses Cas9n as a nuclease because it relies on single nucleic acid chain break resulting in a higher efficiency of clones produced. However, other Cas family nucleases, or familiy of nucleases could be used. Other suitable nucleases, such as Cpf1, zinc finger nucleases, and talens, could be used though additional nucleases with similar properties are in development.

In another embodiment, the invention is a method of using the resulting pluripotent cells, cell derivatives, designer red cells or designer platelets in the laboratory as reagents to test patient blood samples for the presence of antibody. One would do this by using the designer platelets or designer red cells as the source of antigen to then test for binding of patient-derived antibodies from a blood sample. The designer red cell or designer platelet would serve as a solid surface for the patient antibody to bind.

Any blood sample could serve as a source of patient antibody for the purpose of detecting patient antibody titers to a specific platelet alloantigen. In terms of detection and quantification of the patient antibody, methods such as dilution titration, dose response curves, and the use of a secondary antibody directed to the patient antibody known by those of skill in the art could be used. Detection platforms could include enzyme linked immunosorbend assays (ELISAs), western blotting, direct or indirect microscopy, flow cytometry or other methods known in the art.

In another embodiment, the designer red cell or designer platelet would serve as a source of control reagents for either nucleic acid or antigenic analysis. At times, it is difficult to source patients with very rare alloantigens. These patient samples are needed as controls for both nucleic acid or DNA testing of patient materials and for antigenic testing of patient materials.

Definitions

By "blood sample" we mean whole blood, plasma, sera, platelet rich plasma or other products which can be created by fractionating or purifying products from a blood product. This would include but not be limited to such products as cryopresserved blood products or antibody purified from any of the aforementioned blood products. Blood samples could be used as a source of patient antibody.

By "cell type of interest" we mean platelets, red cells, progenitor cells, stem cells, or alloantigens produced by gene editing methods described herein which are then bound to a solid surface such as a bead or microtiter plate to create a cell substitute.

By "designer platelets" we mean a platelet that is the result of genetic editing so that it expresses a specific platelet antigen or group of antigens on its surface, an iPS cell or iPS cell derivative that expresses a specific platelet antigen or group of antigens on its surface, or a platelet antigen from any of the aforementioned cell types that is subsequently bound to a solid surface such as a microtiter plate or bead to create a surface similar to a platelet with respect to platelet antigen expression. Designer platelets could be made to lack expression of HLA or other surface antigens by means of additional gene editing.

By "gene editing" we mean any number of enzyme systems that one could use to perform gene editing which include; CRISPR/Cas (Clustered regularly interspaced short palindrome repeats (CRISPRs)) and CRISPR-associated Zinc-finger nucleases (ZFNs); and transcription-activator-like effector nucleases (TALENs). These are chimeric nucleases composed of programmable, sequence-specific DNA-binding modules linked to a nonspecific DNA cleavage domain.

By "guide sequence" we mean short pieces of RNA complementary to the DNA sequence to be edited which provide both targeting and scaffolding or binding ability for an enzyme.

By "HDR repair oligo" we mean homology-directed repair oligonucleotide to accomplish a template-dependent DNA break repair. By supplying a homology-containing donor template along with a site specific nuclease, HDR faithfully inserts the donor molecule at the targeted locus. This approach enables the insertion of single or multiple transgenes, as well as single nucleotide substitutions as is the case for the alloantigen edits which are the subject of the present application.

By "homology arm" we mean that piece of the repair template that is responsible for pairing targeting the repair template to the portion of DNA to be edited. Homology arms can have varying lengths and are most typically 50-80 bases in length.

By "pluripotent cells" we mean to include cells with the developmental possibility of multiple lineages, including induced pluripotent stem cells, bone marrow, DAMI cells, progenitor cells, human embryonic stem cells, or any cell capable of differentiating and being grown in cell culture.

By "repair template" we mean a piece of DNA which provides the edited DNA to be incorporated into the genome.

EXAMPLES

Human platelet alloantigens (HPAs) reside on functionally important platelet membrane glycoproteins, and are caused by single nucleotide polymorphisms in the genes that encode them. Antibodies that form against HPAs are responsible for several clinically important alloimmune bleeding disorders, including fetal and neonatal alloimmune thrombocytopenia and post-transfusion purpura. The HPA-1a/HPA-1b alloantigen system, also known as the $Pl^{A1}/Pl^{A2}$ Lei polymorphism, is the most frequently implicated HPA among Caucasians, and a single Leu33Pro amino acid polymorphism within the integrin β3 subunit is responsible for generating the HPA-1a/HPA-1b alloantigenic epitopes. HPA-1b/b platelets, like those bearing other low-frequency platelet-specific alloantigens, are relatively rare in the population, and difficult to obtain for purposes of transfusion therapy and diagnostic testing. We employed CRISPR/Cas9 gene editing technology to transform Leu33-positive megakaryocyte-like DAMI cells and induced pluripotent stem (iPS) cells to the Pro33 allotype. CD41-positive megakaryocyte progenitors derived from these cells expressed the HPA-1b ($Pl^{A2}$) alloantigenic epitope, as reported by diagnostic NciI restriction enzyme digestion, DNA sequencing, and western blot analysis using HPA-1b-specific human maternal alloantisera. Application of CRISPR/Cas9 technology to genetically edit this and other clinically-important HPAs holds great potential for production of designer platelets for diagnostic, investigative and ultimately therapeutic use.

In addition to their well-described roles in platelet adhesion and thrombus formation, each of the major human platelet membrane glycoproteins exists in the human gene pool in multiple allelic isoforms, most of which differ from the predominant wild-type allele by only a single amino acid. A subset of these polymorphic isoforms is immunogenic in man—i.e. the three-dimensional structures encompassing the polymorphic amino acid are capable of eliciting an alloimmune response in appropriately mis-matched individuals. The resulting alloantibodies bind to exposed target epitopes on the platelet surface, resulting in rapid clearance from circulation of the opsonized platelets by liver and splenic macrophages (1).

Alloantibodies to platelet-specific antigens are responsible for two clinically-important bleeding disorders: Post-transfusion purpura (PTP) and neonatal alloimmune thrombocytopenia (NAIT—variously referred to in the literature as NATP, FNIT, and FNAIT) (2). PTP is a rare syndrome in which a multiparous woman, after receiving a blood transfusion, enigmatically clears not only the transfused platelets, but her own as well, leading to severe thrombocytopenia, bruising, and petechiae. Unlike PTP, NAIT is a fairly common disorder, complicating 1 in 350 pregnancies (3), and leading to severe fetal and/or neonatal thrombocytopenia in approximately 1 in 1000 births (3, 4). Although many infants recover uneventfully, NAIT is the leading cause of severe thrombocytopenia in the fetus and neonate, often producing bleeding serious enough to require transfusion with "antigen-negative" platelets. The most destructive consequences of NAIT, however, are intracranial hemorrhage and intrauterine death as early as 20-24 weeks of gestation (5). Despite advances in treatment, NAIT remains the leading cause of intracranial hemorrhage in full-term infants (6-10), often leading to life-long disability.

The first human platelet alloantigen system was identified serologically more than 50 years ago and termed Zw (11) or Platelet Antigen 1 ($Pl^{A1}$) (12) respectively. The $Pl^A$ epitope is controlled by a single Leu33Pro amino acid polymorphism within the PSI domain of platelet membrane glycoprotein (GP)IIIa (=the integrin β3 subunit) (13), and work performed in many laboratories since that time has led to the identification of 29 distinct Human Platelet-specific Alloantigen (HPA) systems (HPAs 1-29) on six different glycoproteins (14). $Pl^{A1}$ (HPA-1a), however, remains the alloantigen that most commonly provokes PTP and NAIT, being responsible for ~80% of the cases in which an alloantibody can be detected.

Despite the availability of numerous DNA-based platforms for the rapid genotyping of each of the HPAs (15-19), identification of a platelet alloantigen-specific antibody in the maternal sera is still required to make a positive diagnosis of NAIT (10), and less commonly, for posttransfusion refractoriness (20). Determination of antibody specificity, and in some cases titer, is also critical for guiding prenatal treatment to reduce the likelihood of prenatal bleeding and intracranial hemorrhage in utero, facilitating postnatal management, and managing future pregnancies (10, 21, 22). Platelets bearing low-frequency platelet alloantigens, however, are often difficult or impossible to obtain, and their lack of availability represents a significant barrier for developing effective therapies, and for diagnosing, NAIT. The purpose of the present investigation was to combine recent advances in gene editing and platelet production technologies to generate antigenically-distinct, alloantigen-specific megakaryocyte progenitors for diagnostic and investigative use.

Results

CRISPR-mediated conversion of $Pl^{A1}$ homozygous DAMI cells to $Pl^{A2}$. Because induced pluripotent stem (iPS) cells do not express the GPIIb-IIIa (CD41/CD61) complex unless they are subjected to a rather lengthy differentiation process, conditions for CRISPR-mediated genome editing, including selection of guide RNAs (gRNAs) and homology directed repair (HDR) oligonucleotides, were first optimized using DAMI cells; a human polyploid megakaryocytic cell line that constitutively expresses the common $Pl^{A1}$ allelic isoform of GPIIIa (23).

Figure 2:
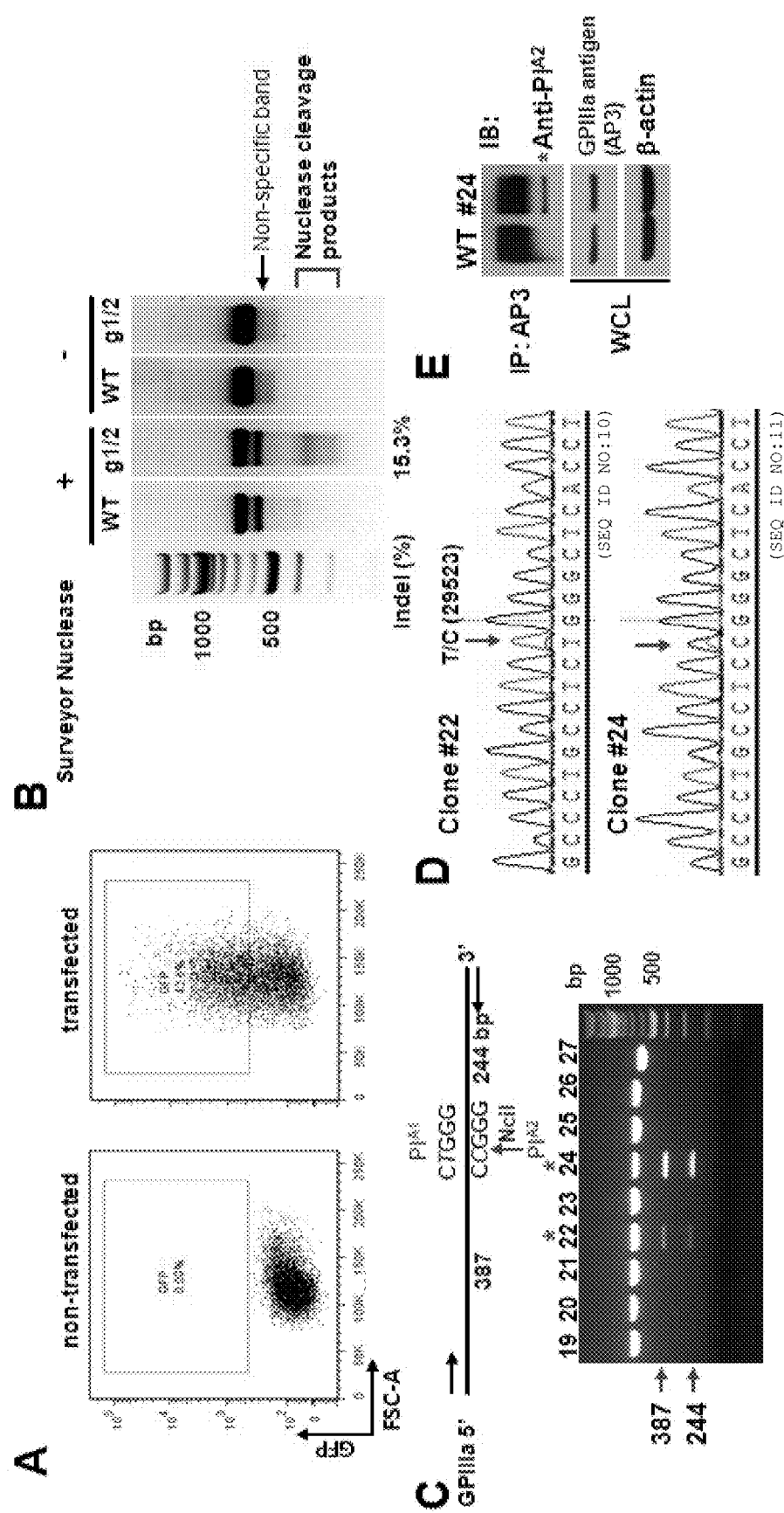
FIG. 2A: Illustrates the conversion of $Pl^{A1}$-homozygous DAMI cells to $Pl^{A2}$ using CRISPR/Cas9n-directed gene editing, specifically, DAMI cells were transfected with px461-gRNA1, px461-gRNA2, and a single-stranded $Pl^{A2}$-encoding HRD repair template using Nucleofection. GFP positive cells, representing ~40% of the total population, were FACS-sorted 24 hrs post transfection, placed into cell culture, and expanded.
FIG. 2B: Illustrates the conversion of $Pl^{A1}$-homozygous DAMI cells to $Pl^{A2}$ using CRISPR/Cas9n-directed gene editing, specifically, genomic DNA from cultured GFP-positive DAMI cells was isolated, PCR-amplified, and analyzed using the Surveyor nuclease. The red bracket indicates the range of expected fragment sizes. Note that the cell population that had been transfected with the two gRNAs shows the presence of insertions/deletions (indels), indicative of Cas9n-mediated cleavage at the $Pl^A$ locus.
FIG. 2C: Illustrates the conversion of $Pl^{A1}$-homozygous DAMI cells to $Pl^{A2}$ using CRISPR/Cas9n-directed gene editing, specifically, genomic DNA from single cell GFP-positive DAMI clones was PCR amplified and digested with NciI to identify those clones encoding the $Pl^{A2}$ allelic isoform of GPIIIa. The red arrows indicate the expected NciI digestion products. Red asterisks indicate $Pl^{A2}$-positive clones #22 and #24.
FIG. 2D: Illustrates the conversion of $Pl^{A1}$-homozygous DAMI cells to $Pl^{A2}$ using CRISPR/Cas9n-directed gene editing, specifically, the ITGB3 locus surrounding the $Pl^{A1}/Pl^{A2}$ polymorphic site was PCR-amplified from genomic DNA of DAMI cell clones #22 and #24 and subjected to DNA sequence analysis, confirming the presence of the HDR-introduced T>C 29523 point mutation. The red arrow highlights the heterozygous partial allelic substitution expected in the multiploid DAMI cell line.
FIG. 2E: Illustrates the conversion of $Pl^{A1}$-homozygous DAMI cells to $Pl^{A2}$ using CRISPR/Cas9n-directed gene editing, specifically, detergent cell lysates from wild-type and clone #24 DAMI cells were immunoprecipitated using the GPIIIa-specific mAb, AP3, followed by immunoblotting with human maternal anti-Pl$^{A2}$ antiserum. The relative equivalence of antigen loading was determined by immunoblotting whole cell lysates (WCL) with AP3 and anti-b-actin antibodies. Note that clone #24, but not wild-type DAMI cells, has a Pl$^{A2}$-reactive band (red asterisk).
Figure 4:
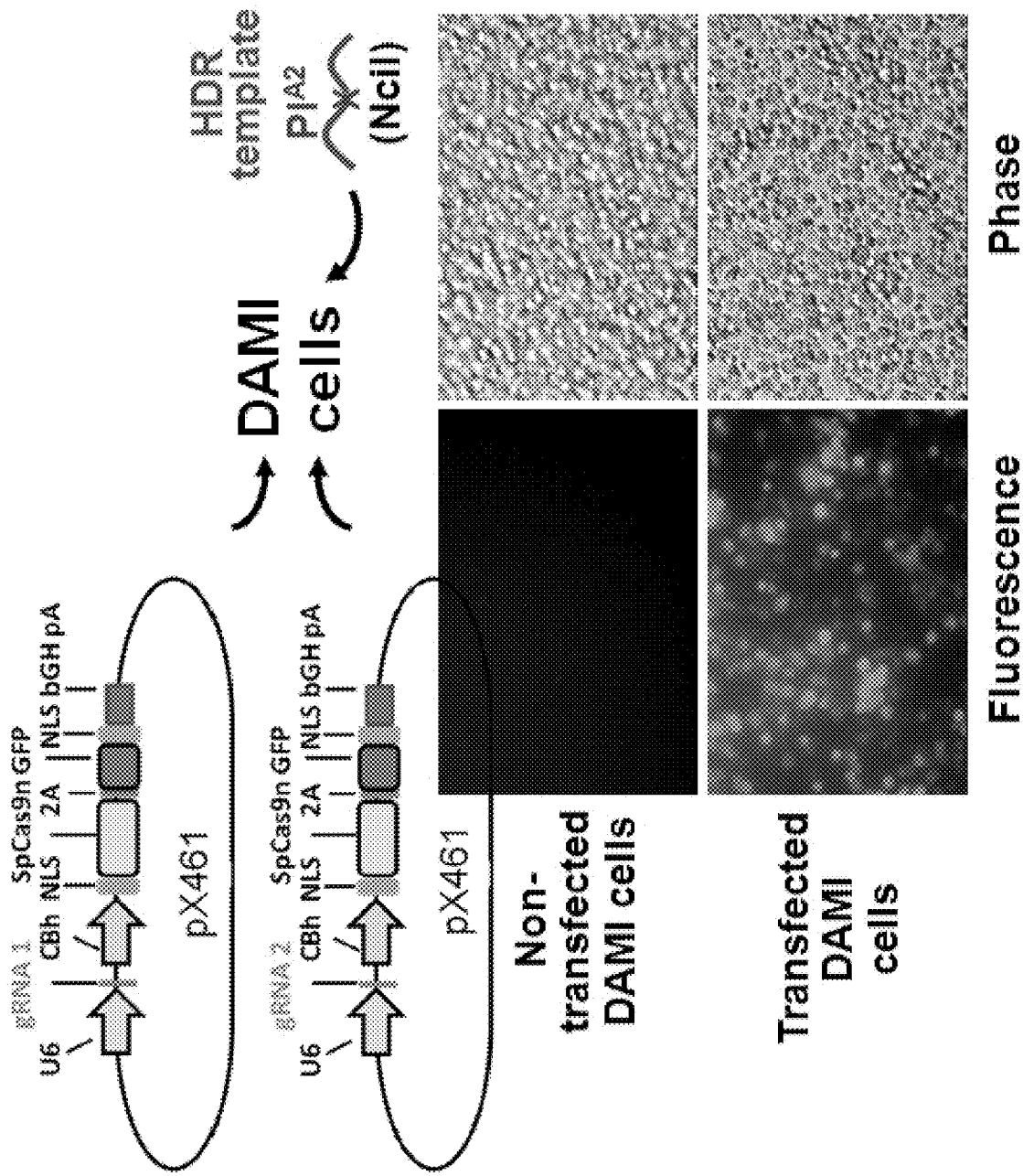
FIG. 4 shows DAMI cells transfected with px461-gRNA1, px461-gRNA2 and Pl$^{A2}$ ssODN using NUCLEOFECTION. Cells were analyzed 24 hrs post transfection using fluorescence and light microscopy.

To convert the $Pl^{A1}$ allelic form of GPIIIa, which differs from $Pl^{A2}$ by a single T29523C nucleotide substitution in the ITGB3 gene, to $Pl^{A2}$, we designed two gRNAs targeting opposite strands of ITGB3 gene (FIG. 1B) and introduced them into px461, which encodes the single-strand nickase Cas9n and green fluorescent protein (GFP) (FIG. 1A). GFP-encoding px461 plasmids harboring each gRNA sequence were transfected into DAMI cells together with a 181 nucleotide $Pl^{A2}$ HDR template (FIG. 4), and the resulting GFP positive cells were sorted by flow cytometry to enrich for transfected cells (FIG. 2A). Following cell expansion, Surveyor nuclease digestion of a genomic DNA hybridized/re-hybridized PCR amplicon spanning the Cas9n cleavage site revealed partial cleavage products of 270-371 bp (FIG. 2B), indicating efficient gRNA-directed double nicking by Cas9n. Genomic DNA from 27 GFP-positive single cell clones was digested with NciI, revealing two clones (#22 and #24) that carried the $Pl^{A2}$ polymorphism (FIG. 2C).

DNA sequence analysis (FIG. 2D) confirmed heterozygous replacement of the $Pl^{A2}$ HDR template in these cells. Based on the band intensity of the NciI cleavage products, it appears that approximately half of the $Pl^{A1}$ alleles in clone #24 were CRISPR-converted to $Pl^{A2}$, while only one fourth were converted in clone #22—expected due to the polyploid nature of the DAMI cell population. Finally, immunoprecipitation/western blot analysis using a well-characterized human anti-$Pl^{A2}$ maternal alloantiserum demonstrated that at least a subpopulation of GPIIIa molecules from clone #24 now expresses the Pro33, $Pl^{A2}$ alloantigenic epitope (FIG. 2E).

Figure 3:
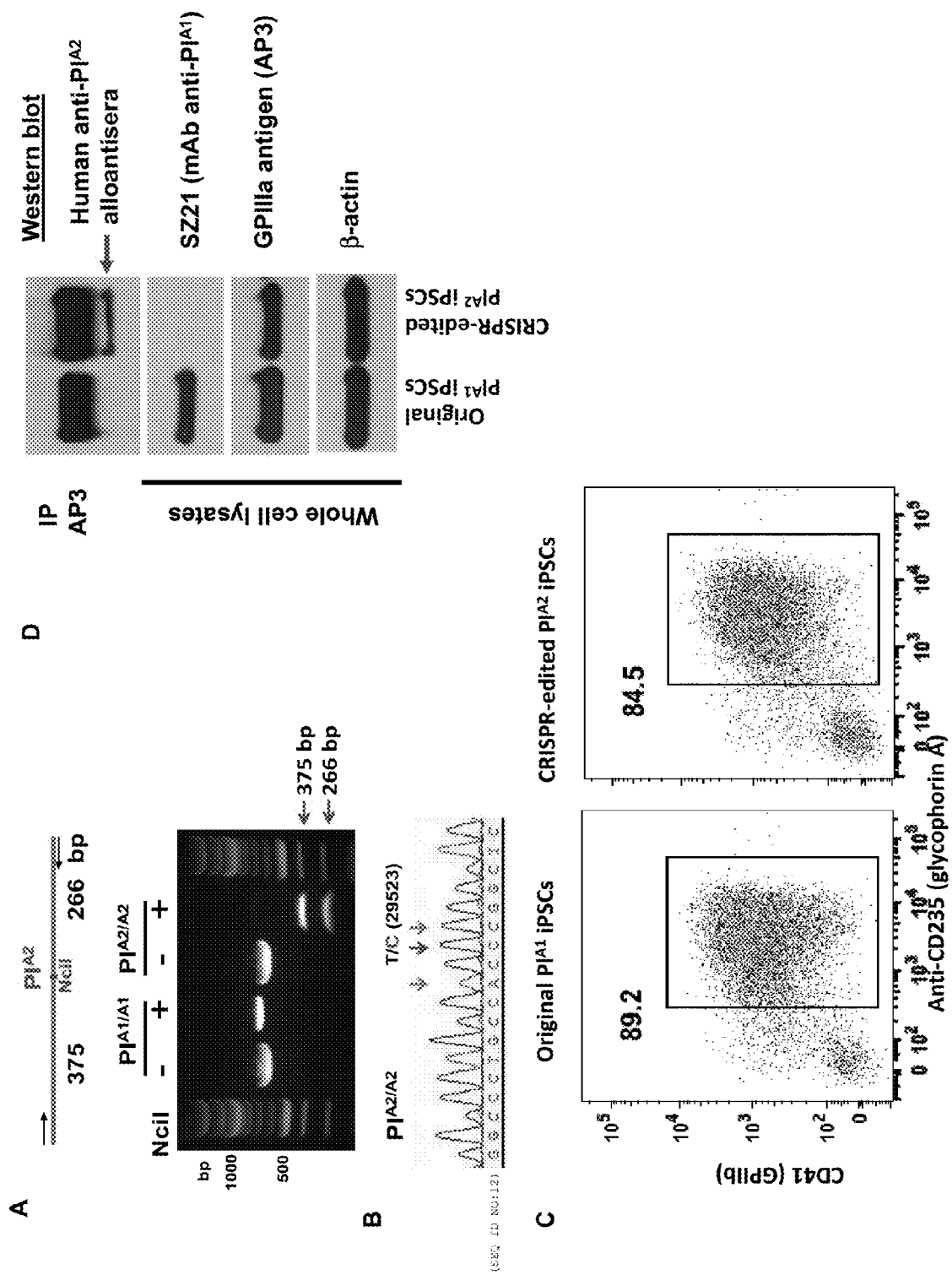
FIG. 3A: Illustrates the conversion of iPS cells from Pl$^{A1}$ to Pl$^{A2}$, specifically, schematic of the diagnostic PCR reaction used to genotype the iPSCs. The NciI restriction enzyme site differentiates the Pl$^{A1}$ allelic isoform from Pl$^{A2}$. Genomic DNA, isolated from iPS cells that had been transfected with px462-gRNA1, px462-gRNA2 and Pl$^{A2}$ ssODN and selected with puromycin, was PCR amplified and digested with NciI. Red arrows indicate the expected fragment sizes of a typical clone that had been converted to Pl$^{A2}$.
FIG. 3B: Illustrates the conversion of iPS cells from Pl$^{A1}$ to Pl$^{A2}$, specifically, sequencing data confirmed the T>C 29523 point mutation in CRISPR-edited Pl$^{A2}$ iPSCs. The red arrow indicates the target T>C mutation. The blue arrows indicate silent mutations that were intentionally introduced into the repair oligo to prevent digestion of the final edited genome by Cas9n.
FIG. 3C: Illustrates the conversion of iPS cells from Pl$^{A1}$ to Pl$^{A2}$, specifically, allele-specific expression of GPIIb-IIIa (CD41) on both native and CRISPR-edited iPSC-derived day 8 hematopoietic progenitor cells. Non-adherent HPCs express abundant levels of the CD41/CD61 complex (integrin αIIb-β3) as well as CD235 (glycophorin A). Note that both cell lines were similarly double-positive.
FIG. 3D: Illustrates the conversion of iPS cells from Pl$^{A1}$ to Pl$^{A2}$, specifically, cell lysates from wild-type, Pl$^{A1}$-positive and CRISPR-edited Pl$^{A2}$ iPSC-derived HPCs were immunoprecipitated with AP3, followed by immunoblotting with human maternal anti-Pl$^{A2}$ antiserum. Note that the anti-Pl$^{A2}$ antiserum is positive for GPIIIa expressed in the gene-edited, but not native, iPS cell line (red arrow), while the Pl$^{A1}$-specific mAb, SZ21, binds GPIIIa from native, but not gene-edited, iPS cells. Loading was evaluated by blotting with AP3 and anti-β-actin, as described in FIG. 2.

$Pl^{A1}$ to $Pl^{A2}$ conversion of human iPS cells. Having optimized the conditions for editing the ITGB3 locus in DAMI cells, we applied a similar protocol to edit iPS.K3 cells—a footprint-free cell line that was reprogrammed from human foreskin fibroblasts with non-episomal plasmids (24). DNA sequencing (not shown) of genomic DNA of iPS.K3 cells in and around the $Pl^{A}$ polymorphism showed them to be homozygous for the $Pl^{A1}$ allele. gRNAs 1 and 2 were cloned into the CRISPR/Cas9 vector, px462, which expresses a puromycin resistance gene (FIG. 1A) and cotransfected with the $Pl^{A2}$ HDR template into iPS.K3 cells using Nucleofection. Clones from puromycin-resistant colonies were manually picked and expanded two weeks post-plating and subjected to diagnostic NciI restriction enzyme digestion to identify clones in which biallelic conversion of $Pl^{A1}$ to $Pl^{A2}$ had taken place. FIG. 3A shows the NciI digestion pattern of one such homozygous $Pl^{A2}$ clone, the T>C 29523 genotype of which was verified by DNA sequencing (FIG. 3B).

Wild-type $Pl^{A1}$ homozygous iPS.K3 cells and their CRISPR-edited progeny were then differentiated into hematopoietic progenitor cells (HPCs) using a previously-described serum-free, feeder-free, adherent differentiation system (25, 26). The HPCs generated with this method possess erythroid, megakaryocyte, and myeloid multi-lineage potential, and co-express the CD41/CD61 GPIIb-IIIa complex, as well as CD235 (glycophorin A). As shown in FIG. 3C, HPCs from both iPS cell lines express similar levels of CD41+ and CD235+ on their surface, demonstrating importantly that the CRISPR-modified cells retained full ability to differentiate. Finally, GPIIIa from the $Pl^{A2}$, but not wild-type, iPS cell line expressed the $Pl^{A2}$ allelic isoform of GPIIIa, as shown by its specific reactivity with a human anti-$Pl^{A2}$ alloantiserum, and its concomitant loss of SZ21 binding (FIG. 3D). Taken together, these data demonstrate successful CRISPR-mediated homozygous conversion of $Pl^{A1}$ to $Pl^{A2}$ human iPS cells and their subsequent differentiation into GPIIb-IIIa-expressing HPCs.

Figure 5:
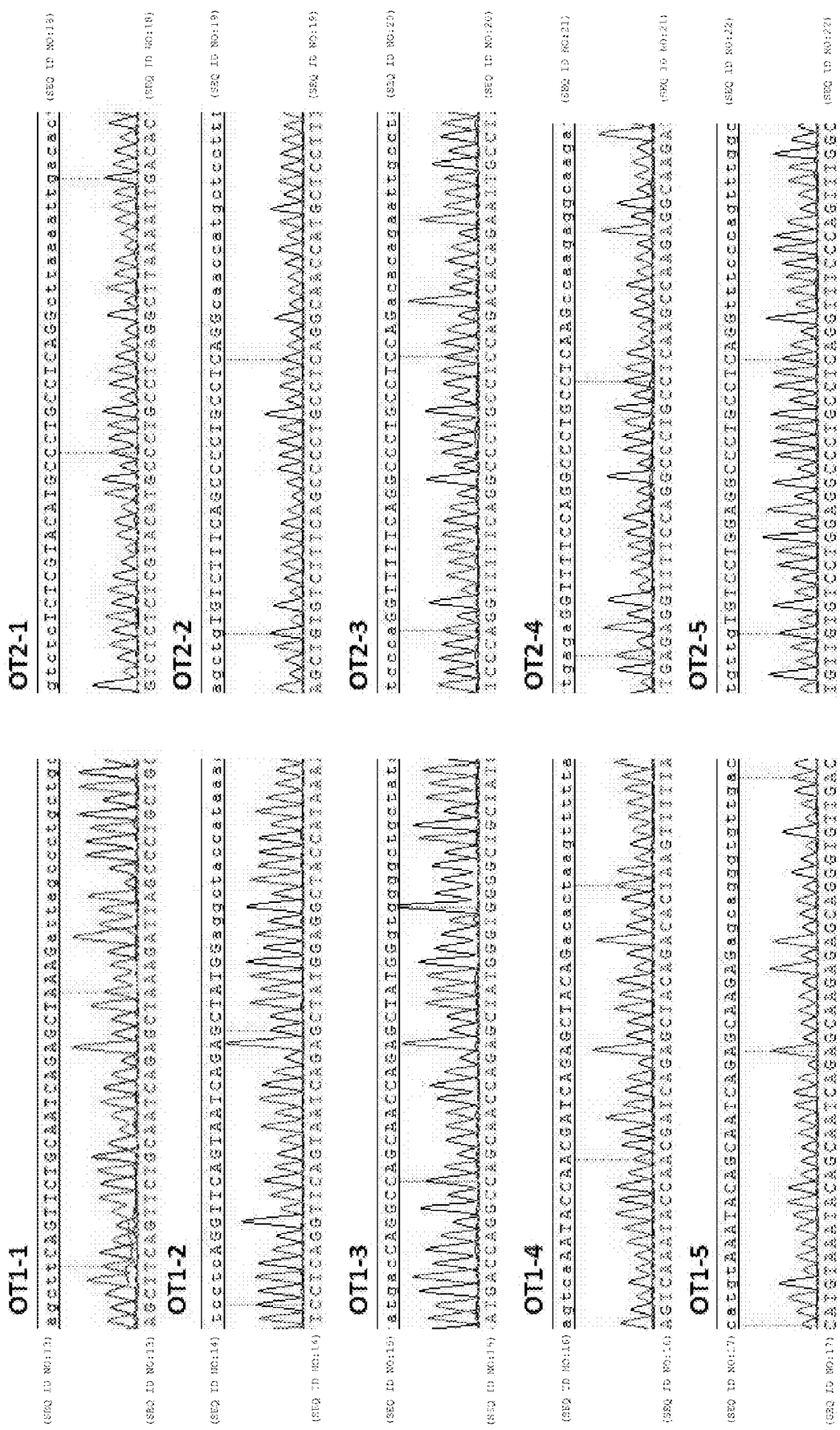
FIG. 5 illustrates off-target analysis of gRNA1 and gRNA2. Top five putative off-target sites for gRNA1 and gRNA2 were PCR amplified from CRISPR-edited Pl$^{A2}$ iPS.K3 genomic DNA and directly sequenced. The possible off-target sequences were shown at the sixth to twenty eighth bases, as indicated by the capital letters above the sequencing peaks.

An unintended consequence of CRISPR/Cas9 technology is the occasional introduction of off-target mutations elsewhere in the genome that may affect cell growth and differentiation. This problem can be mitigated in part by using a single-strand Cas9 nickase in combination with two different gRNAs that target opposite strands surrounding the sequence to be edited (FIG. 1B). To evaluate putative off-target effects of the pair of the guide sequences used in this study, we PCR-amplified the top five off-target sites predicted for each of our guide sequences (FIG. 6) in our $Pl^{A2}$ iPS.K3 cell line, but found no mutations at these loci (FIG. 5).

Discussion

Despite the availability of genotyping for platelet-specific alloantigens, platelet immuno-diagnostics continues to be hampered by the technical complexities of HPA antibody detection—still the gold standard in making a clinical diagnosis of NAIT. Though the majority of human platelet alloantigenic determinants have now been characterized, platelets expressing them are often unavailable, and their detection is additionally hampered by instability or loss of the epitopes following detergent solubilization and storage (27). Finally, serological typing is complicated by the fact that ~25% of multiparous women produce antibodies against Class I Human Leukocyte Antigens (HLA) (28) that mask detection of platelet-specific alloantigenic epitopes. Taken together, laboratories charged with resolving difficult cases of NAIT have struggled to translate basic scientific discoveries into improved clinical care of families afflicted by this serious condition. The goal of the present investigation, therefore, was to exploit the convergence of CRISPR/Cas9 gene editing and iPS cell→platelet technologies to create human platelet progenitors expressing low-frequency platelet alloantigens for diagnostic, investigative, and perhaps future therapeutic, use.

In 2007, the Yamanaka (29, 30) and Thomson (31) labs reported that adult human fibroblasts can be reprogrammed, using a limited number of transcription factors, into pluripotent stem cells. Building upon this discovery, several groups have developed efficient protocols for differentiating iPS cells to HPCs (32, 33), that can be expanded to megakaryocytes (34, 35), and platelets (36-38). While still a long way off from producing a transfusable number of platelets, the ability to generate and cryopreserve iPS cell-derived megakaryocyte progenitor cells leaves open the possibility of maintaining an inexhaustible source of platelets and their progenitors for diagnostic and investigative applications. We sought to exploit this capability to produce antigenically-distinct megakaryocytes and progenitor cells from genetically-customized iPS cells in sufficient quantities for characterization of their platelet-specific alloantigen expression and function by flow cytometry and other diagnostic methods.

Originally discovered as an ancient form of adaptive immunity that functions by incorporating short pieces of DNA into a series of clustered, regularly interspaced short palindromic repeats within the genomes of bacteria and archaea to direct degradation of foreign DNA (39), the CRISPR system of RNA-guided nucleases has largely supplanted earlier zinc finger and TALEN protein-guided nucleases as the preferred gene-editing tool (40). By incorporating a carefully-designed gRNA sequence into a plasmid or lentiviral vector encoding a Cas nuclease, one can engineer double-(41) or single-(42) strand breaks at precise endogenous loci within the genome of almost any cell that can be transfected or transduced, including iPS cells (43), embryonic stem cells, and zygotes (44).

In the present investigation, we combined these technologies to generate iPS cell-derived HPCs that express allele-specific forms of clinically-important human platelet alloantigens. Because it is the most frequent cause of NAIT and PTP in the western world, we performed proof-of-concept genetic manipulations on the Pl$^A$ alloantigen system, and were able to successfully generate sufficient quantities of Pl$^{A1}$- and Pl$^{A2}$-specific HPCs to perform flow cytometric detection of these human platelet alloantigens—an assay that requires less than ten microliters of human serum. Intact human cells are normally not used for alloantibody detection because maternal sera containing platelet antigen-specific alloantibodies also often contain antibodies specific for Class I HLA that are present on the platelet surface (45, 46). For this reason, time-consuming and technically-demanding antigen-capture ELISA assays are necessary that require hundreds of microliters of maternal alloantisera. HLA detection can be circumvented by introducing a stop codon into the $\beta_2$ microglobulin ($\beta$2M) gene that encodes the light chain of Class I HLA molecules, which is required for trafficking of all Class I heavy chains to the cell surface (47).

This tactic has been achieved using both siRNA technology in CD34+ hematopoietic stem cells (48) and TALEN technology in iPS cells (37) to produce HLA Class I-deficient platelets, and we have recently employed CRISPR technology to generate a $\beta$2M-negative founder iPS line (not shown) into which we plan to introduce polymorphisms that define each of the major human platelet alloantigens. The availability of a potentially replenishable source of alloantigen-specific megakaryocyte and platelet progenitors should go a long way towards improving the diagnosis, treatment and care of patients suffering from this all-to-common cause of morbidity and mortality in newborns.

Methods

Guide RNA plasmid constructs. gRNAs were designed using the CRISPR Design Tool to minimize off-target effects and selected to precede a 5'-NGG protospacer-adjacent motif (PAM). gRNAs used in this study were: gRNA1: 5'-AAGTCCAGCAATCAGAGCTA-3' (SEQ ID NO:1), gRNA2: 5'-TGTCTTACAGGCCCTGCCTC3' (SEQ ID NO:2). Oligos were annealed and cloned into the BbsI site of the Cas9 expression plasmids px461 or px462 (Addgene, Cambridge, Mass.).

Single-stranded homology-directed repair (HDR) template. A single-stranded oligo-deoxynucleotide (ssODN), 181 nucleotides in length, having the sequence 5'-ACTCGGGCCTCACTCACTGGGAACTCGATGGAT-TCTGGGGCACAGTTATCCTTCAGCAGATT CTCCT-TCAGGTCACAGCGAGGTGAGCCGGGTGGCAGGGC-CTGTAAGACAGGAGCCCAAAGA GAAGTCCAGCAATCAGAGCTATGCCGACTCTCTAC-CTCCTGCAGGCCCTACCACTTCC-3' (SEQ ID NO:3) was synthesized by Integrated DNA Technologies (IDT, Coralville, Iowa). This oligo corresponds to the antisense strand, and in addition to containing the CTG→CCG Pl$^{A1}$ to Pl$^{A2}$ substitution, also contains silent mutations within the recognition sequence and the PAM sequence, of gRNA2 to avoid repetitive digestions by Cas9n.

Cell lines and transfection. $2\times10^6$ DAMI cells were cultured at 37° C. in 5% CO2 in Iscove's Modified Dulbecco's Medium (IMDM) with 10% horse serum, penicillin (100 U/ml) and streptomycin (100 µg/ml) and transfected with 1 µg of each guide plasmid and 40 pmol of the ssODN HDR template using the Amaxa cell line Nucleofector Kit C (Lonza, Allendale, N.J.) and Nucleofector Program X-005. Transfection efficiency was assessed by visualizing GFP expression using fluorescence microscopy.

Human iPS.K3 cells (24) (kind gift of Dr. Steven Duncan, Medical College of Wisconsin) were grown on StemAdhere Defined Matrix-coated plates (Stemcell Technologies, Vancouver, BC) in mTeSR1/MEF conditioned medium (50:50) containing 4 ng/ml bFGF (Thermo Fisher Scientific, Grand Island, N.Y.) at 37° C. in 4% O2/5% CO2. After incubation with 10 µM ROCK inhibitor Y27632 (StemRD Inc. Burlingame, Calif.), $2\times10^5$ cells were transfected with 0.5 µg of each guide plasmid and 40 pmol of the HDR oligonucleotide using the Amaxa P3 primary cell 4D Nucleofector Kit (Lonza) and Nucleofector Program CB-150. The cells were then plated on DR4 MEF feeder cells supplemented with 10 µM Y27632. 24-hour post-transfection puromycin was applied at a concentration of 1 µg/ml for 24 hr. Single clones were harvested at 12 to 14 days post-puromycin-selection and re-plated on StemAdhere-coated plates. Karyotyping of the iPSC lines was performed by Dynacare Laboratories (Milwaukee, Wis.) after genotyping to identify the correct lines and every 15 passages routinely during culture.

Differentiation of iPS.K3 cells. Wild-type iPS.K3 cells and CRISPR-edited Pl$^{A2}$ iPS.K3 cells were differentiated to HPCs as previously described (25, 26). Briefly, cells were cultured in feeder-free conditions prior to plating on Matrigel for differentiation. The medium and cytokine changes were followed as described with the following modification. The GSK-3β inhibitor, CHIR99021 (Cayman, Ann Arbor, Mich.) (0.5-1 µM) was used instead of Wnt3a. Cells were cultured at 37° C., 5% CO$_2$, 5% O$_2$ and 90% N$_2$ for 7-9 days and loosely adherent HPCs were collected by carefully removing the supernatant. Cells were analyzed by flow cytometry for the surface expression of CD41a and CD235a.

Flow cytometry. 24 hrs post-transfection, DAMI cells were washed and resuspended in growth medium containing 25 mM HEPES buffer and filtered through 100 µm MACS SmartStrainers (Miltenyi Biotec, San Diego, Calif.). GFP$^+$ cells were analyzed with a BD Biosciences (San Jose, Calif.) ARIA-IIIu Cell Sorter. Non-transfected cells were used as negative control. GFP+ cells were sorted as single cells into individual wells of 96-well plates. Analysis of iPSC-derived HPCs was performed using a CANTO Flow Cytometer (Becton Dickinson, San Jose, Calif.). The antibodies used were anti-CD235-APC and CD41a-PE (BD Biosciences). Flow cytometry data were analyzed using FLOWJO software (Tree Star Inc., Ashland, Oreg.).

Detection of introduced mutations in genomic DNA. Cells were harvested 72 hrs after transfection, and DNA was extracted using a QIAamp DNA mini kit (Qiagen, Germantown, Md.) according to the manufacture's protocol. The genomic region flanking the $Pl^{A1}$ site was amplified using PCR primer GPIIIa fw2: 5'-CGTGGAATTCGCTGGTC-TACCAGGCATCTT-3' (SEQ ID NO:4) and GPIIIa rev2: 5'-CCGAAGCTTACCTTGTGCTCTATGCCCAC-3' (SEQ ID NO:5). PCR products were purified using QIAquick Spin Column (QIAGEN). Purified PCR products (400 ng) were mixed with 1× Taq DNA polymerase PCR buffer, denatured at 95° C. and reannealed to form DNA heteroduplexes. The reannealed PCR products were treated with Surveyor nuclease (IDT) following the manufacturer's protocol and analyzed on a 2% agarose gel. Quantification was based on relative band intensities. The percentage of DNA mismatches was determined by the formula $100 \times \{1-[1-(b+c)/(a+b+c)]^{1/2}\}$, wherein a is the integrated intensity of the undigested PCR product and b and c are the integrated intensities of each cleavage product.

Genotyping. Genomic DNA was extracted from each clone of DAMI and iPS.K3 cells using the QUICKEXTRACT DNA Extraction Solution (Epicenter, Madison, Wis.) following the manufacture's protocol. The region surrounding the $Pl^{A1}/Pl^{A2}$ polymorphism was amplified using GPIIIa fw1: 5'-CGTGGAATTCGGCATCTTACTG-TACAGGCT-3' (SEQ ID NO:6) and GPIIIa rev1: 5'-GGCAAGCTTA-AGACTTCCTCCTCAGACCT-3' (SEQ ID NO:7). PCR products were purified using QIAquick Spin Column, digested with NciI (New England Biolabs Inc., Ipswich, Mass.), and analyzed on 2% agarose gels.

Immunoprecipitation and Western blot analysis. $2 \times 10^7$ DAMI cells or $3 \times 10^6$ iPSC-derived HPCs were lysed in 20 mM Tris (pH7.4), 150 mM NaCl, 1% Triton X-100, 1 mM EDTA, 10 mM N-ethylmaleimide and protease inhibitor cocktail (Thermo Fisher Scientific). Lysates were centrifuged at 17,000×g for 15 min at 4° C. Supernatants were collected, precleared with protein G sepharose and then incubated with the anti-GPIIIa monoclonal antibody (mAb) AP3 overnight at 4° C. Immune complexes were collected on protein G sepharose beads, eluted with nonreducing SDS sample buffer, and loaded onto 4-20% polyacrylamide gels. Following electrophoresis, the samples were electrotransferred onto PVDF membrane (EMD Millipore, Billerica, Mass.) and immunoblotted with either human anti-$Pl^{A2}$ antisera, the $Pl^{A1}$-selective murine mAb, SZ21 (Beckman Coulter, Brea, Calif.), AP3, or a mouse mAb specific for β-actin (Sigma, St. Louis, Mo.). Bound antibodies were visualized using species-specific peroxidase-conjugated donkey anti-human IgG (H+L) or goat anti-mouse IgG (H+L) secondary antibodies from Jackson ImmunoResearch Laboratories (West Grove, Pa.).

REFERENCES

1. Aster R H. Studies of the fate of platelets in rats and man. Blood. 1969; 34(2):117-28.
2. Newman P J, McFarland J G, and Aster R H. In: Loscalzo J, and Schafer A I eds. Thrombosis and Hemorrhage. Lippincott Williams and Wilkins; 2003:441-56.
3. Williamson L M, Hackett G, Rennie J, Palmer C R, Maciver C, Hadfield R, Hughes D, Jobson S, and Ouwehand W H. The natural history of fetomaternal alloimmunization to the platelet-specific antigen HPA-1a (PlA1, Zwa) as determined by antenatal screening. Blood. 1998; 92(7):2280-7.
4. Kjeldsen-Kragh J, Killie M K, Tomter G, Golebiowska E, Randen I, Hauge R, Aune B, Oian P, Dahl L B, Pirhonen J, et al. A screening and intervention program aimed to reduce mortality and serious morbidity associated with severe neonatal alloimmune thrombocytopenia. Blood. 2007; 110(3):833-9.
5. Giovangrandi Y, Daffos F, Kaplan C, Forestier F, Mac A J, and Moirot M. Very early intracranial haemorrhage in alloimmune fetal thrombocytopenia. Lancet. 1990; 336 (8710):310.
6. Bonacossa I A, and Jocelyn L J. Alloimmune thrombocytopenia of the newborn: neurodevelopmental sequelae. Am J Perinatol. 1996; 13(4):211-5.
7. Dreyfus M, Kaplan C, Verdy E, Schlegel N, Durand-Zaleski I, and Tchernia G. Frequency of immune thrombocytopenia in newborns: a prospective study Immune Thrombocytopenia Working Group. Blood. 1997; 89(12): 4402-6.
8. Spencer J A, and Burrows R F. Feto-maternal alloimmune thrombocytopenia: a literature review and statistical analysis. The Australian & New Zealand journal of obstetrics & gynaecology. 2001; 41(1):45-55.
9. Turner M L, Bessos H, Fagge T, Harkness M, Rentoul F, Seymour J, Wilson D, Gray I, Ahya R, Cairns J, et al. Prospective epidemiologic study of the outcome and cost-effectiveness of antenatal screening to detect neonatal alloimmune thrombocytopenia due to anti-HPA-1a. Transfusion. 2005; 45(12):1945-56.
10. Bussel J. Diagnosis and management of the fetus and neonate with alloimmune thrombocytopenia. Journal of thrombosis and haemostasis: JTH. 2009; 7 (Suppl 1):253-7.
11. van Loghem J J, Dorfmeyer H, van der Hart H, and Schreuder F. Serological and genetical studies on a platelet antigen (Zw). Vox Sang. 1959; 4(2):161-9.
12. Shulman N R, Aster R H, Pearson H A, and Hiller M C. Immunoreactions involving platelets. V I. Reactions of maternal isoantibodies responsible for neonatal purpura. Differentiation of a second platelet antigen system. The Journal of clinical investigation. 1962; 41(5):1059-69.
13. Newman P J, Derbes R S, and Aster R H. The human platelet alloantigens, $Pl^{A1}$ and $Pl^{A2}$, are associated with a leucine33/proline33 amino acid polymorphism in membrane glycoprotein IIIa, and are distinguishable by DNA typing. JClinInvest. 1989; 83(5):1778-81.
14. Metcalfe P, Watkins N A, Ouwehand W H, Kaplan C, Newman P, Kekomaki R, De Haas M, Aster R, Shibata Y, Smith J, et al. Nomenclature of human platelet antigens. Vox Sang. 2003; 85(3):240-5.
15. McFarland J G, Aster R H, Bussel J B, Gianopoulos J G, Derbes R S, and Newman P J. Prenatal diagnosis of neonatal alloimmune thrombocytopenia using allele-specific oligonucleotide probes. Blood. 1991; 78(9):2276-82.
16. Curtis B R. Genotyping for human platelet alloantigen polymorphisms: applications in the diagnosis of alloimmune platelet disorders. Seminars in thrombosis and hemostasis. 2008; 34(6):539-48.

17. Le Toriellec E, Chenet C, and Kaplan C. Safe fetal platelet genotyping: new developments. Transfusion. 2013; 53(8):1755-62.
18. An Q X, Li C Y, Xu L J, Zhang X Q, Bai Y J, Shao Z J, and Zhang W. High-throughput simultaneous genotyping of human platelet antigen-1 to -16 by using suspension array. Transfusion. 2013; 53(11):2722-8.
19. Skogen B, Bellissimo D, Hessner M J, Santoso S, Aster R H, Newman P J, and McFarland J G. Rapid determination of platelet alloantigen genotypes by polymerase chain reaction using allele specific primers. Transfusion. 1994; 34(11):955-60.
20. Vassallo R R, Jr. New paradigms in the management of alloimmune refractoriness to platelet transfusions. Current opinion in hematology. 2007; 14(6):655-63.
21. Bussel J B, and Sola-Visner M. Current approaches to the evaluation and management of the fetus and neonate with immune thrombocytopenia. Seminars in perinatology. 2009; 33(1):35-42.
22. Pacheco L D, Berkowitz R L, Moise K J, Jr., Bussel J B, McFarland J G, and Saade G R. Fetal and neonatal alloimmune thrombocytopenia: a management algorithm based on risk stratification. Obstetrics and gynecology. 2011; 118(5):1157-63.
23. Wilcox D A, Olsen J C, Ishizawa L, Griffith M, and White G C, 2nd. Integrin aIIb promoter-targeted expression of gene products in megakaryocytes derived from retrovirus-transduced human hematopoietic cells. Proceedings of the National Academy of Sciences of the United States of America. 1999; 96(17):9654-9.
24. Si-Tayeb K, Noto F K, Sepac A, Sedlic F, Bosnjak Z J, Lough J W, and Duncan S A. Generation of human induced pluripotent stem cells by simple transient transfection of plasmid DNA encoding reprogramming factors. BMC developmental biology. 2010; 10:81.
25. Mills J A, Paluru P, Weiss M J, Gadue P, and French D L. In: Qu KDBaC-K ed. Methods in Molecular Biology. New York: Springer Science+Business Media; 2014:181-94.
26. Paluru P, Hudock K M, Cheng X, Mills J A, Ying L, Galvao A M, Lu L, Tiyaboonchai A, Sim X, Sullivan S K, et al. The negative impact of Wnt signaling on megakaryocyte and primitive erythroid progenitors derived from human embryonic stem cells. Stem cell research. 2014; 12(2):441-51.
27. Harrison C R, Curtis B R, McFarland J G, Huff R W, and Aster R H. Severe neonatal alloimmune thrombocytopenia caused by antibodies to human platelet antigen 3a (Baka) detectable only in whole platelet assays. Transfusion. 2003; 43(10):1398-402.
28. Ouwehand W H. The dilemma of screening for antibodies against low-frequency human platelet antigens. Transfusion. 2005; 45(3):288-9.
29. Takahashi K, Tanabe K, Ohnuki M, Narita M, Ichisaka T, Tomoda K, and Yamanaka S. Induction of pluripotent stem cells from adult human fibroblasts by defined factors. Cell. 2007; 131(5):861-72.
30. Ohnuki M, Takahashi K, and Yamanaka S. Generation and characterization of human induced pluripotent stem cells. Current protocols in stem cell biology. 2009; Chapter 4:Unit 4A 2.
31. Yu J, Vodyanik M A, Smuga-Otto K, Antosiewicz-Bourget J, Frane J L, Tian S, Nie J, Jonsdottir G A, Ruotti V, Stewart R, et al. Induced pluripotent stem cell lines derived from human somatic cells. Science. 2007; 318 (5858):1917-20.
32. Choi K D, Vodyanik M A, and Slukvin, I I. Generation of mature human myelomonocytic cells through expansion and differentiation of pluripotent stem cell-derived lin-CD34+CD43+CD45+ progenitors. The Journal of clinical investigation. 2009; 119(9):2818-29.
33. Kennedy M, D'Souza S L, Lynch-Kattman M, Schwantz S, and Keller G. Development of the hemangioblast defines the onset of hematopoiesis in human ES cell differentiation cultures. Blood. 2007; 109(7):2679-87.
34. Sullivan S K, Mills J A, Koukouritaki S B, Vo K K, Lyde R B, Paluru P, Zhao G, Zhai L, Sullivan L M, Wang Y, et al. High-level transgene expression in induced pluripotent stem cell-derived megakaryocytes: correction of Glanzmann thrombasthenia. Blood. 2014; 123(5):753-7.
35. Nakamura S, Takayama N, Hirata S, Seo H, Endo H, Ochi K, Fujita K, Koike T, Harimoto K, Dohda T, et al. Expandable megakaryocyte cell lines enable clinically applicable generation of platelets from human induced pluripotent stem cells. Cell stem cell. 2014; 14(4):535-48.
36. Thon J N, Mazutis L, Wu S, Sylman J L, Ehrlicher A, Machlus K R, Feng Q, Lu S, Lanza R, Neeves K B, et al. Platelet bioreactor-on-a-chip. Blood. 2014; 124 (12): 1857-67
37. Feng Q, Shabrani N, Thon J N, Huo H, Thiel A, Machlus K R, Kim K, Brooks J, Li F, Luo C, et al. Scalable generation of universal platelets from human induced pluripotent stem cells. Stem Cell Reports. 2014; 3(5):817-31.
38. Wang Y, Hayes V, Jarocha D, Sim X, Harper D C, Fuentes R, Sullivan S K, Gadue P, Chou S T, Torok-Storb B J, et al. Comparative analysis of human ex vivo-generated platelets vs megakaryocyte-generated platelets in mice: a cautionary tale. Blood. 2015; 125(23):3627-36.
39. Karginov F V, and Hannon G J. The CRISPR system: small RNA-guided defense in bacteria and archaea. Molecular cell. 2010; 37(1):7-19.
40. Mali P, Esvelt K M, and Church G M. Cas9 as a versatile tool for engineering biology. Nature methods. 2013; 10(10):957-63.
41. Cong L, Ran F A, Cox D, Lin S, Barretto R, Habib N, Hsu P D, Wu X, Jiang W, Marraffini L A, et al. Multiplex genome engineering using CRISPR/Cas systems. Science. 2013; 339(6121):819-23.
42. Ran F A, Hsu P D, Wright J, Agarwala V, Scott D A, and Zhang F. Genome engineering using the CRISPR-Cas9 system. Nature protocols. 2013; 8(11):2281-308.
43. Ding Q, Regan S N, Xia Y, Oostrom L A, Cowan C A, and Musunuru K. Enhanced efficiency of human pluripotent stem cell genome editing through replacing TALENs with CRISPRs. Cell stem cell. 2013; 12(4):393-4.
44. Wang H, Yang H, Shivalila C S, Dawlaty M M, Cheng A W, Zhang F, and Jaenisch R. One-step generation of mice carrying mutations in multiple genes by CRISPR/Cas-mediated genome engineering. Cell. 2013; 153(4): 910-8.
45. Nielsen L S, and Svejgaard A. H L-A immunization and H L-A types in pregnancy. Tissue Antigens. 1972; 2(4): 316-27.
46. Aster R H, Szatkowski N, Liebert M, and Duquesnoy R J. Expression of HLA-B12, HLA-B8, w4, and w5 on platelets. TransplantProc. 1977; 9(4):1695-6.
47. Lancet D, Parham P, and Strominger J L. Heavy chain of HLA-A and HLA-B antigens is conformationally labile: a possible role for b2-microglobulin. Proceedings of the National Academy of Sciences of the United States of America. 1979; 76(8):3844-8.

48. Gras C, Schulze K, Goudeva L, Guzman C A, Blasczyk R, and Figueiredo C. HLA-universal platelet transfusions prevent platelet refractoriness in a mouse model. Human gene therapy. 2013; 24(12):1018-28.
49. Ran F A, Hsu P D, Lin C Y, Gootenberg J S, Konermann S, Trevino A E, Scott D A, Inoue A, Matoba S, Zhang Y, et al. Double nicking by RNA-guided CRISPR Cas9 for enhanced genome editing specificity. Cell. 2013; 154(6): 1380-9.
50. Shen B, Zhang W, Zhang J, Zhou J, Wang J, Chen L, Wang L, Hodgkins A, Iyer V, Huang X, et al. Efficient genome modification by CRISPR-Cas9 nickase with minimal off-target effects. Nature methods. 2014; 11(4): 399-402.

We claim:

1. A method of creating a mammalian hematopoietic progenitor cell expressing a specific platelet alloantigen by combining gene editing techniques and cell culture differentiation or expansion techniques employing pluripotent cells, the method comprising the steps of:

a) providing one or more guide RNAs designed to target the ITGB3 gene around the $Pl^A$ locus;

b) ligating the guide RNA of step (a) into a plasmid which also expresses a Cas9 nuclease;

c) transfecting mammalian $\beta_2$ microglobulin-deficient induced pluripotent stem cells with the plasmid of step (b) in the presence of a homology-directed repair (HDR) template oligo encoding a single nucleotide substitution specific to alloantigen HPA-1;

d) cloning and selecting resulting clones that express the HPA-1 alloantigen; and e) differentiating the selected clones into mammalian hematopoietic progenitor cells that express the HPA-1 alloantigen.

2. The method of claim 1 wherein the nuclease is Cas9n.

3. Mammalian hematopoietic progenitor cells created by the method of claim 1.

4. The method of claim 1, wherein the HDR template oligo additionally encodes a diagnostic restriction enzyme site at the target locus.

5. The method of claim 1, wherein the plasmid additionally expresses a selectable marker.

6. The method of claim 1, wherein the plasmid additionally expresses a reporter gene.

7. The method of claim 1, wherein the mammalian $\beta_2$ microglobulin-deficient induced pluripotent stem cells are produced using one or more guide RNAs targeting the areas flanking the $\beta_2$ microglobulin gene of HLA and a Cas9n nuclease in mammalian induced pluripotent stem cells.

8. The method of claim 6, wherein the reporter gene is GFP.

9. The method of claim 4, wherein the diagnostic restriction enzyme site is a NciI restriction site.

* * * * *

UNITED STATES PATENT AND TRADEMARK OFFICE
CERTIFICATE OF CORRECTION

PATENT NO. : 10,725,041 B2  
APPLICATION NO. : 14/931321  
DATED : July 28, 2020  
INVENTOR(S) : Peter Jay Newman et al.

Page 1 of 1

It is certified that error appears in the above-identified patent and that said Letters Patent is hereby corrected as shown below:

In the Specification

Column 11, Line 64-65, "$Pl^{A1}/Pl^{A2}$ Lei polymorphism" should be -- $Pl^{A1}/Pl^{A2}$ polymorphism --.

Signed and Sealed this  
Twenty-second Day of September, 2020

Andrei Iancu  
*Director of the United States Patent and Trademark Office*

SEQUENCE LISTING

```
<160> NUMBER OF SEQ ID NOS: 54

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
aagtccagca atcagagcta                                                     20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tgtcttacag gccctgcctc                                                     20

<210> SEQ ID NO 3
<211> LENGTH: 181
<212> TYPE: DNA
<213> ORGANISM: Artificial Sequence
<220> FEATURE:
<223> OTHER INFORMATION: Synthetic

<400> SEQUENCE: 3
actcgggcct cactcactgg gaactcgatg gattctgggg cacagttatc cttcagcaga         60
ttctccttca ggtcacagcg aggtgagccg ggtggcaggg cctgtaagac aggagcccaa        120
agagaagtcc agcaatcaga gctatgccga ctctctacct cctgcaggcc ctaccacttc        180
c                                                                        181

<210> SEQ ID NO 4
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 4
cgtggaattc gctggtctac caggcatctt                                          30

<210> SEQ ID NO 5
<211> LENGTH: 29
<212> TYPE: DNA
<213> ORGANISM: Artificial Sequence
<220> FEATURE:
<223> OTHER INFORMATION: Synthetic PCR primer

<400> SEQUENCE: 5
ccgaagctta ccttgtgctc tatgcccac                                           29
```

<210> SEQ ID NO 6
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 6
cgtggaattc ggcatcttac tgtacaggct                               30

<210> SEQ ID NO 7
<211> LENGTH: 29
<212> TYPE: DNA
<213> ORGANISM: Artificial Sequence
<220> FEATURE:
<223> OTHER INFORMATION: Synthetic PCR primer

<400> SEQUENCE: 7
ggcaagctta agacttcctc ctcagacct                                29

<210> SEQ ID NO 8
<211> LENGTH: 87
<212> TYPE: DNA
<213> ORGANISM: Homo sapiens

<400> SEQUENCE: 8
ggaggtagag agtcgccata gctctgattg ctggacttct ctttgggctc ctgtcttaca    60
ggccctgcct ctgggctcac ctcgctg                                       87

<210> SEQ ID NO 9
<211> LENGTH: 87
<212> TYPE: DNA
<213> ORGANISM: Homo sapiens

<400> SEQUENCE: 9
cctccatctc tcagcggtat cgagactaac gacctgaaga gaaacccgag gacagaatgt   60
ccgggacgga gacccgagtg gagcgac                                       87

<210> SEQ ID NO 10
<211> LENGTH: 21
<212> TYPE: DNA
<213> ORGANISM: Homo sapiens

<400> SEQUENCE: 10
gccctgcctc tgggctcacc t                                         21

<210> SEQ ID NO 11
<211> LENGTH: 21
<212> TYPE: DNA
<213> ORGANISM: Homo sapiens

<400> SEQUENCE: 11
gccctgcctc cgggctcacc t                                         21

<210> SEQ ID NO 12
<211> LENGTH: 18
<212> TYPE: DNA
<213> ORGANISM: Homo sapiens

<400> SEQUENCE: 12
ggccctgcca cccggctc                                             18

<210> SEQ ID NO 13
<211> LENGTH: 42
<212> TYPE: DNA
<213> ORGANISM: Homo sapiens

<400> SEQUENCE: 13
agcttcagtt ctgcaatcag agctaaagat tagccctgct gc                          42

<210> SEQ ID NO 14
<211> LENGTH: 41
<212> TYPE: DNA
<213> ORGANISM: Homo sapiens

<400> SEQUENCE: 14
tcctcaggtt cagtaatcag agctatggag gctaccataa a                           41

<210> SEQ ID NO 15
<211> LENGTH: 41
<212> TYPE: DNA
<213> ORGANISM: Homo sapiens

<400> SEQUENCE: 15
atgaccaggc cagcaaccag agctatgggt ggggctgcta t                           41

<210> SEQ ID NO 16
<211> LENGTH: 42
<212> TYPE: DNA
<213> ORGANISM: Homo sapiens

<400> SEQUENCE: 16
agtcaaatac caacgatcag agctacagac actaagtttt ta                          42

<210> SEQ ID NO 17
<211> LENGTH: 42
<212> TYPE: DNA
<213> ORGANISM: Homo sapiens

<400> SEQUENCE: 17
catgtaaata cagcaatcag agcaagagag cagggtgttg ac                          42

<210> SEQ ID NO 18
<211> LENGTH: 42
<212> TYPE: DNA
<213> ORGANISM: Homo sapiens

<400> SEQUENCE: 18
gtctctctcg tacatgccct gcctcaggct taaaattgac ac                          42

<210> SEQ ID NO 19
<211> LENGTH: 43
<212> TYPE: DNA
<213> ORGANISM: Homo sapiens

<400> SEQUENCE: 19
agctgtgtct ttcagcccct gcctcaggca accatgctcc ttt                         43

<210> SEQ ID NO 20
<211> LENGTH: 42
<212> TYPE: DNA
<213> ORGANISM: Homo sapiens

<400> SEQUENCE: 20
tcccaggttt ttcaggccct gcctccagac acagaattgc ct                          42

```
<210> SEQ ID NO 21
<211> LENGTH: 41
<212> TYPE: DNA
<213> ORGANISM: Homo sapiens

<400> SEQUENCE: 21
tgagaggttt tccaggccct gcctcaagcc aagaggcaag a                    41

<210> SEQ ID NO 22
<211> LENGTH: 42
<212> TYPE: DNA
<213> ORGANISM: Homo sapiens

<400> SEQUENCE: 22
tgttgtgtcc tggaggccct gcctcaggtt tcccagtttg gc                   42

<210> SEQ ID NO 23
<211> LENGTH: 23
<212> TYPE: DNA
<213> ORGANISM: Homo sapiens

<400> SEQUENCE: 23
aagtccagca atcagagcta tgg                                        23

<210> SEQ ID NO 24
<211> LENGTH: 23
<212> TYPE: DNA
<213> ORGANISM: Homo sapiens

<400> SEQUENCE: 24
cagttctgca atcagagcta aag                                        23

<210> SEQ ID NO 25
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 25
gagaaccatc aacccaatgc                                            20

<210> SEQ ID NO 26
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 26
gtgtatggca gtttgtccac                                            20

<210> SEQ ID NO 27
<211> LENGTH: 23
<212> TYPE: DNA
<213> ORGANISM: Homo sapiens

<400> SEQUENCE: 27
aggttcagta atcagagcta tgg                                        23

<210> SEQ ID NO 28
<211> LENGTH: 21
<212> TYPE: DNA
```

```
<213> ORGANISM: Artificial Sequence
<220> FEATURE:
<223> OTHER INFORMATION: Synthetic PCR primer

<400> SEQUENCE: 28
gccataaagt gggatcattt g                                        21

<210> SEQ ID NO 29
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 29
accataggtc tcctcgatgt                                          20

<210> SEQ ID NO 30
<211> LENGTH: 23
<212> TYPE: DNA
<213> ORGANISM: Homo sapiens

<400> SEQUENCE: 30
caggccagca accagagcta tgg                                      23

<210> SEQ ID NO 31
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 31
tcaatgctaa acaacggcac                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 32
gctgctgatc tgaaagggta                                          20

<210> SEQ ID NO 33
<211> LENGTH: 23
<212> TYPE: DNA
<213> ORGANISM: Homo sapiens

<400> SEQUENCE: 33
aataccaacg atcagagcta cag                                      23

<210> SEQ ID NO 34
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 34
caactgagcc tttcctacca                                          20

<210> SEQ ID NO 35
<211> LENGTH: 20
```

```
<212> TYPE: DNA
<213> ORGANISM: Artificial Sequence
<220> FEATURE:
<223> OTHER INFORMATION: Synthetic PCR primer

<400> SEQUENCE: 35
agagacggaa ttgagacacc                                              20

<210> SEQ ID NO 36
<211> LENGTH: 23
<212> TYPE: DNA
<213> ORGANISM: Homo sapiens

<400> SEQUENCE: 36
aaatacagca atcagagcaa gag                                          23

<210> SEQ ID NO 37
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 37
attaaagctt ctgctggcga                                              20

<210> SEQ ID NO 38
<211> LENGTH: 21
<212> TYPE: DNA
<213> ORGANISM: Artificial Sequence
<220> FEATURE:
<223> OTHER INFORMATION: Synthetic PCR primer

<400> SEQUENCE: 38
tgatactcca cctgacaact c                                            21

<210> SEQ ID NO 39
<211> LENGTH: 23
<212> TYPE: DNA
<213> ORGANISM: Homo sapiens

<400> SEQUENCE: 39
tgtcttacag gccctgcctc tgg                                          23

<210> SEQ ID NO 40
<211> LENGTH: 23
<212> TYPE: DNA
<213> ORGANISM: Homo sapiens

<400> SEQUENCE: 40
tctcgtacat gccctgcctc agg                                          23

<210> SEQ ID NO 41
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 41
ctgtctctgc tgcacatcta                                              20

<210> SEQ ID NO 42
<211> LENGTH: 20
<212> TYPE: DNA
```

```
<213> ORGANISM: Artificial Sequence
<220> FEATURE:
<223> OTHER INFORMATION: Synthetic PCR primer

<400> SEQUENCE: 42
gttcaggtgg agacaggaat                                              20

<210> SEQ ID NO 43
<211> LENGTH: 23
<212> TYPE: DNA
<213> ORGANISM: Homo sapiens

<400> SEQUENCE: 43 tgtcttttcag ccctgcctc agg                                          23

<210> SEQ ID NO 44
<211> LENGTH: 23
<212> TYPE: DNA
<213> ORGANISM: Artificial Sequence
<220> FEATURE:
<223> OTHER INFORMATION: Synthetic PCR primer

<400> SEQUENCE: 44
taagaccata tggacatggc aga                                          23

<210> SEQ ID NO 45
<211> LENGTH: 21
<212> TYPE: DNA
<213> ORGANISM: Artificial Sequence
<220> FEATURE:
<223> OTHER INFORMATION: Synthetic PCR primer

<400> SEQUENCE: 45
gagtagcaaa tggctggaac a                                            21

<210> SEQ ID NO 46
<211> LENGTH: 23
<212> TYPE: DNA
<213> ORGANISM: Homo sapiens

<400> SEQUENCE: 46 ggttttttcag gccctgcctc cag                                         23

<210> SEQ ID NO 47
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 47
gagtttgctg tgcagagatg                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 48
tgcttaagtg tgggccttta                                              20

<210> SEQ ID NO 49
<211> LENGTH: 23
```

```
<212> TYPE: DNA
<213> ORGANISM: Homo sapiens

<400> SEQUENCE: 49
ggttttccag gccctgcctc aag                                             23

<210> SEQ ID NO 50
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 50
aaagagagat gagctcgtgg                                                 20

<210> SEQ ID NO 51
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 51
tttcaagagt ggagtggctt                                                 20

<210> SEQ ID NO 52
<211> LENGTH: 23
<212> TYPE: DNA
<213> ORGANISM: Homo sapiens

<400> SEQUENCE: 52
tgtcctggag gccctgcctc agg                                             23

<210> SEQ ID NO 53
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 53
gaaattcttt ggccacctcc                                                 20

<210> SEQ ID NO 54
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 54
cacagtgcca aatatcagca                                                 20
```